US006806089B1

(12) United States Patent
Lakowicz et al.

(10) Patent No.: US 6,806,089 B1
(45) Date of Patent: Oct. 19, 2004

(54) LOW FREQUENCY MODULATION SENSORS USING NANOSECOND FLUOROPHORES

(75) Inventors: Joseph R. Lakowicz, Ellicott City, MD (US); Ignacy Gryczynski, Baltimore, MD (US)

(73) Assignee: University of Maryland, Baltimore, Baltimore, MD (US)

(*) Notice: Subject to any disclaimer, the term of this patent is extended or adjusted under 35 U.S.C. 154(b) by 0 days.

(21) Appl. No.: 09/786,627

(22) PCT Filed: Sep. 8, 1999

(86) PCT No.: PCT/US99/20370
§ 371 (c)(1),
(2), (4) Date: Apr. 17, 2001

(87) PCT Pub. No.: WO00/14515
PCT Pub. Date: Mar. 16, 2000

Related U.S. Application Data

(60) Provisional application No. 60/099,499, filed on Sep. 8, 1998.

(51) Int. Cl.[7] .............................................. G01N 21/64
(52) U.S. Cl. ......................... 436/68; 436/79; 436/172; 436/74; 436/95; 600/316; 600/317
(58) Field of Search ........................... 436/536, 74, 79, 436/68, 163, 172, 93–95; 250/459.1; 600/316, 317; 422/82.07, 82.08

(56) References Cited

U.S. PATENT DOCUMENTS

| | | | |
|---|---|---|---|
| 5,030,832 A | | 7/1991 | Williams et al. |
| 5,246,867 A | * | 9/1993 | Lakowicz et al. ............. 436/95 |
| 5,315,993 A | * | 5/1994 | Alcala ........................ 128/634 |
| 5,448,992 A | | 9/1995 | Kupershmidt |
| 5,527,684 A | | 6/1996 | Mabile et al. |
| 5,624,847 A | * | 4/1997 | Lakowicz et al. ............. 436/68 |
| 5,631,169 A | * | 5/1997 | Lakowicz et al. .......... 436/537 |
| 5,648,269 A | * | 7/1997 | Lakowicz et al. ............. 436/68 |
| 5,770,454 A | | 6/1998 | Essenpreis et al. |
| 6,051,437 A | * | 4/2000 | Luo et al. ................... 436/172 |
| 6,190,612 B1 | * | 2/2001 | Berger et al. ............ 422/82.07 |
| 6,306,661 B1 | * | 10/2001 | Lakowicz et al. .......... 436/138 |

OTHER PUBLICATIONS

Shabbir B. Bambot et al., "Sensing oxygen through skin using a red diode laser and fluorescence lifetimes," Biosensors & Bioelectronics 10(6/7):643–652 (1995).
Felix N. Castellano et al., "Long–Lifetime Ru(II) Complexes as Labeling Reagents for Sulfhydryl Groups," Analytical Biochemistry 255:165–170 (1998).
Enrico Gratton et al., "Resolution of Mixtures of Fluorophores Using Variable–Frequency Phase and Modulation Data," Biophys. J. 46:479–486 (Oct. 1984).
Ignacy Gryczynski et al., "Effects of Light Quenching on the Emission Spectra and Intensity Decays of Fluorophore Mixtures," J. of Fluorescence 7(3):167–183 (1997).
Xiang–Qun Guo et al., "A Long–Lived, Highly Luminescent Re(I) Metal–Ligand Complex as a Biomolecular Probe," Analytical Biochemistry 254: 179–186 (1997).

Xiang–Qun Guo et al., "Use of a Long–Lifetime Re(I) Complex in Fluorescence Polarization Immnuoassays of High–Molecular–Weight Analytes," Anal. Chem. 70(3):632–637 (Feb. 1, 1998).
Nectarios Klonis et al., "Spectral Properties of Fluorescein in Solvent–Water Mixtures: Applications as a Probe of Hydrogen Bonding Environments in Biological Systems," Photochemistry and Photobiology 67(5):500–510 (1998).
Joseph R. Lakowicz et al., "Frequency–Domain Fluorescence Spectroscopy," Topics in Fluorescence Spectroscopy, vol. 1: Techniques, pp. 293–335, Plenum Press, New York, 1991.
Joseph R. Lakowicz et al., "Construction and Performance of a Variable–Frequency Phase–Modulation Fluorometer," Biophysical Chemistry 21:61–78 (1985).
Joseph R. Lakowicz et al., "Analysis of Fluorescence Decay Kinetics From Variable–Frequency Phase Shift and Modulation Data," Biophys. J. 46:463–477 (Oct. 1984).
Joseph R. Lakowicz et al., "Emerging Biomedical and Advanced Applications of Time–Resolved Fluorescence Spectroscopy," Journal of Fluorescence 4(1):117–136 (1994).
Joseph R. Lakowicz et al., "Metal–ligand complexes as a new class of long–lived fluorophores for protein hydrodynamics and fluorescence polarization immunoassay," Proc. SPIE vol. 2388:32–41 (1995).
Max E. Lippitsch et al., "Luminescence lifetime–based sensing: new materials, new devices," Sensors and Actuators B 38–39:96–102 (1997).
Lisa Randers–Eichhorn et al., "On–line Green Fluorescent Protein Sensor with LED Excitation," Biotechnology and Bioengineering 55(6):921–926 (1997).
Jeffrey Sipior et al., "Single quantum well light emitting diodes demonstrated as excitation sources for nanosecond phase–modulation fluorescence lifetime measurements," Rev. Sci. Instrum. 67(11):3795–3798 (Nov. 1996).

(List continued on next page.)

Primary Examiner—Jeffrey R. Snay
(74) Attorney, Agent, or Firm—Sughrue Mion, PLLC

(57) ABSTRACT

Described is a new approach to fluorescence sensing based on a mixture of fluorophores, one of which is sensitive to the desired analyte. If a long lifetime analyte-insensitive fluorophore is mixed with a short lifetime analyte-sensitive fluorophore, the modulation of the emission at conveniently low frequencies becomes equal to the fractional fluorescence intensity of the sensing fluorophore. Under these conditions the modulation can be used to determine the analyte concentration. This can be used with any fluorophore which changes intensity in response to analyte, and does not require the sensing fluorophore to display a change in lifetime. The feasibility of modulation-based sensing was demonstrated using mixtures of 6-carboxyfluorescein and $[Ru2,2'(bipyridyl)_3]^{2+}$ as a pH sensor and of the calcium probe Fluo-3 and $[Ru2,2'(bipyridyl)_3]^{2+}$ as a calcium sensor.

38 Claims, 28 Drawing Sheets

OTHER PUBLICATIONS

Jeffrey Sipior et al., "Blue light–emitting diode demonstrated as an ultraviolet excitation source for nanosecond phase–modulation fluorescence lifetime measurements," Rev. Sci. Instrum. 68(7):2666–2670 (1997).

Henryk Szmacinski et al., "Frequency–Domain lifetime measurements and sensing in highly scattering media," Sensors and Acutators B 30:207–215 (1996).

E. Gratton et al., "A Continuously Variable Frequency Cross–Correlation Phase Fluorometer with Picosecond Resolution," Biophys. J. 44:315–324 (Dec. 1983).

C. Hutchinson et al., "Fluorescence Lifetime–Based Sensing in Tissues: A Computational Study," Biophys. J. 68:1574–1582 (Apr. 1995).

H. Szmacinski et al., "Lifetime–Based Sensing," in Topics in Fluorescence Spectroscopy: vol 4: Probe Design and Chemical Sensing (JR Lakowicz, Ed.), Plenum Press, New York, pp. 295–334 (1994).

\* cited by examiner

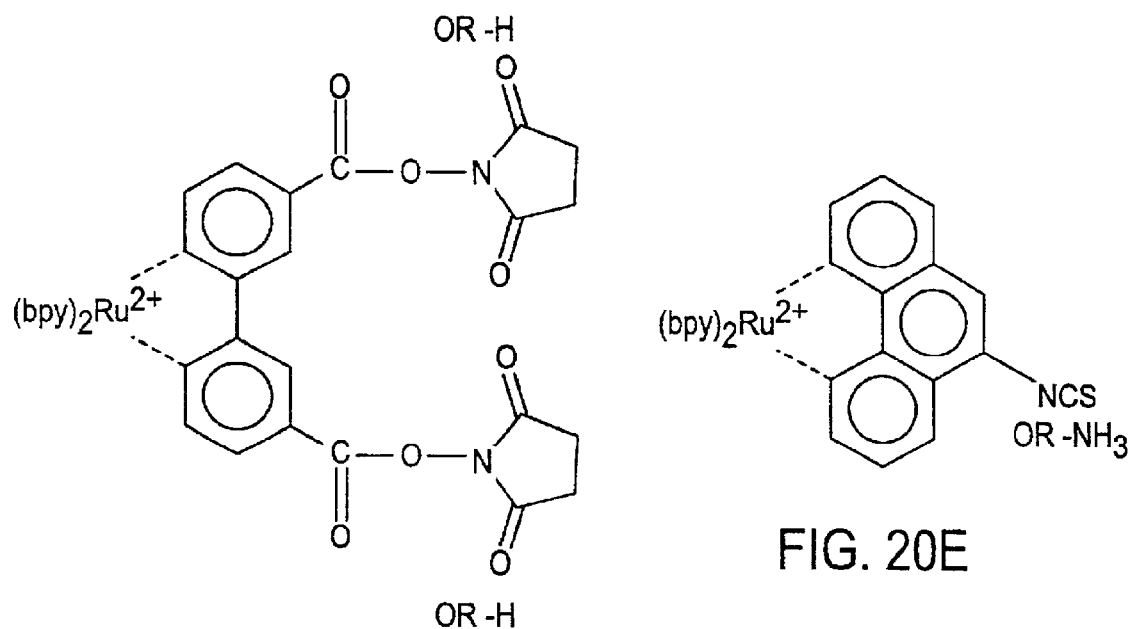
FIG. 20D
FIG. 20E
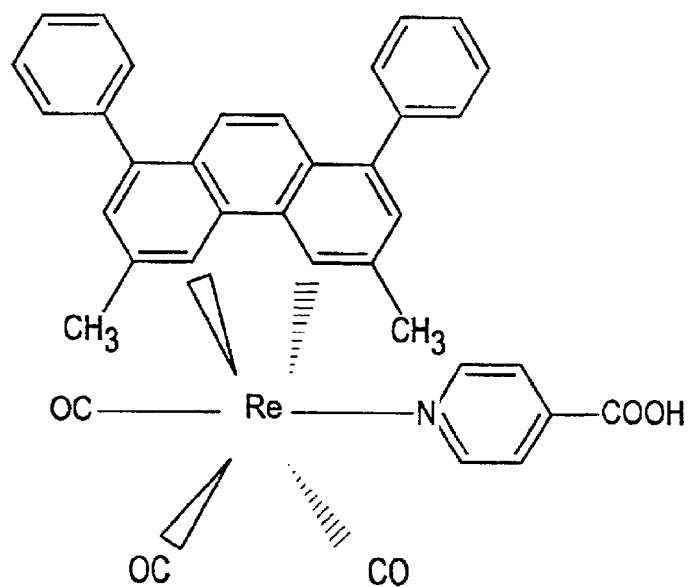
FIG. 20F

LOW FREQUENCY MODULATION SENSORS USING NANOSECOND FLUOROPHORES

This application is a provisional of Ser. No. 60/099,499 filed on Sep. 8, 1998.

This application was made with Government support under Grant No. RR-08119 from the National Institutes of Health National Center for Research Resources. The federal government may have certain rights in this invention.

BACKGROUND OF THE INVENTION

Fluorescence is widely used in analytical and clinical chemistry (Schulman, 1993; Spichiger-Keller, 1998; Wolfbeis, 1991a; Wolfbeis, 1991b; Kunz. 1996; Lakowicz, 1994a; Thompson, 1997). In the past several years there has been increasing interest in the use of time-resolved fluorescence as an analytical tool, e.g., for non-invasive sensing (Szmacinski and Lakowicz, 1994a; Lippitsch et al., 1997; Lippitsch et al., 1988; Bambot et al., 1995; Spichiger-Keller, 1998; Fraser, 1997). The basic idea is to identify fluorophores or sensing schemes in which the decay time of the sample changes in response to the analyte, and to use the decay time to determine the analyte concentration. Such lifetime-based sensing is most often performed using the phase-modulation method. The use of phase angles or decay times rather than intensities is advantageous because decay times are mostly independent of the signal level and can be measured in turbid media and even through skin (Bambot et al., 1995; Szmacinski and Lakowicz, 1996).

Most fluorophores used for sensing display decay times on the nanosecond timescale. It now appears possible to design low cost instruments for sensors with ns decay times. For instance, it is known that blue and UV light emitting diodes (LEDs) can be modulated to over 100 MHz and used as the excitation source in phase-modulation fluorometry (Sipior et al., 1997; Sipior et al., 1996; Lakowicz et al., 1994a; Randers-Eichorn et al., 1997). However, it may be useful to avoid the use of frequencies near 100 MHz which are needed for ns decay time measurements, and thus use the simpler electronics for lower frequencies. Also, a significant fraction of sensing fluorophores display changes in intensity without changes in lifetime.

What are the advantages of low frequency modulation sensing? It is now accepted that lifetime-based sensing can be preferable to intensity-based sensing because the lifetimes are mostly independent of changes in probe concentration and/or signal level. Modulation sensing shows many of these advantages. The modulation will be independent of the total signal level. Hence, modulation sensing can be accurate even if the overall signal level changes due to flexing in fiber optics or changes in the positioning of the sample. However, it is necessary that the relative proportions of the short and long lifetime fluorophores remain the same. If the relative intensities change, in a manner independent of analyte concentration, then the modulation calibration curve will also change. Hence, the calibration curves for a modulation sensor will change if the sensing and reference fluorophore photobleach at different rates.

An advantage of low frequency modulation sensing is the simple instrumentation One can imagine simple hand-held instruments for modulation intensity measurements (FIG. 1). It is now well known that light emitting diodes can be easily modulated at frequencies up to 100 MHz (Sipior et al., 1997; Sipior et al., 1996; Lakowicz et al., 1994a; Randers-Eichorn et al., 1997). Also, LEDs are available within a range of output wavelengths, even down to the near UV at 390 nm (Sipior et al., 1997). LEDs consume little power and can easily be driven by batteries. Hence, the modulation sensor could be a small device held near the skin. The long-lifetime complex can be part of the device, so none of the long-lifetime probe enters the sample or tissue. The high chemical and photochemical stability of the metal-ligand complexes suggests the signal from the long lifetime reference will be constant for long periods of time. Hence, such devices may prove valuable for quantitation of intrinsic and extrinsic fluorophores in tissues.

Additionally, there has been considerable progress in the design and synthesis of long lifetime metal-ligand complexes. Ruthenium, osmium and rhenium complexes have been reported (Lakowicz et al., 1995; Terpetschnig et al., 1997; Castellano et al., 1998). The rhenium complexes are particularly useful in that they display high quantum yields and lifetimes up to 3 $\mu$s in oxygenated solution (Guo et al., 1998; Guo et al., 1997).

And finally, the most important advantage of modulation sensing may be the expanded range of analytes. Any sensing fluorophore which changes intensity can be used in this model. A change in probe lifetime is not needed. Hence, modulation sensing can be used with probes such as a sodium-binding benzofuran isophthalate (SBFI) and a potassium-binding benzofuran isophthalate (PBFI), which are poor wavelength-ratiometric probes for sodium and potassium.

The possibility of non-invasive sensing is based on the low absorbance of tissue at red and near-infrared (NIR) wavelengths, and the increasing availability of long wavelength fluorophores (Lakowicz, 1994b; Matsuoka, 1990; Leznoff and Lever, 1989). However, it is difficult to perform intensity measurements in highly scattering media (Oelkrug, 1994), which has led to interest in the use of time-resolved fluorescence and lifetime-based sensing for non-invasive fluorometry (Szmacinski and Lakowicz, 1994a; Hutchinson et al., 1995; Szmacinski and Lakowicz, 1994b). It is now known that fluorescence lifetimes can be measured in the presence of extensive light scattering, and can even be measured through skin (Bambot et al., 1995).

The publications and other materials used herein to illuminate the background of the invention or provide additional details respecting the practice, are incorporated by reference, and for convenience are respectively grouped in the appended List of References.

SUMMARY OF THE INVENTION

Described here is a new method which allows quantitative measurements of fluorescence intensity with simple instrumentation. The method is self-calibrating related to a reference fluorophore. The method can also be used in highly scattering media. The measurement principle is based on observing the emission from both the fluorophore of interest with a ns decay time and of a reference fluorophore which displays a much longer microsecond lifetime. The reference fluorophore is placed on rather than in the sample to mimic a sensing device with the long lifetime reference held against the skin. The amplitude modulation of the emission is observed using the standard method of frequency-domain fluorometry. At an intermediate modulation frequency, the modulation is equivalent to the fractional intensity of the ns fluorophore. The method was tested in 0.5% intralipid, which is more highly scattering than skin. Quantitative intensity measurements were obtained for various concentrations of fluorescein in intralipid, and of the pH sensor 6carboxy fluorescein. Low frequency modulation measurements provide a general method for quantitative measurements in the presence of factors which preclude direct intensity measurements, or applications which require simple internally referenced measurements.

BRIEF DESCRIPTION OF THE FIGURES

FIGS. 20A–L show representative fluorophores which are not sensitive to analytes.

DETAILED DESCRIPTION OF THE INVENTION

Figure 1:
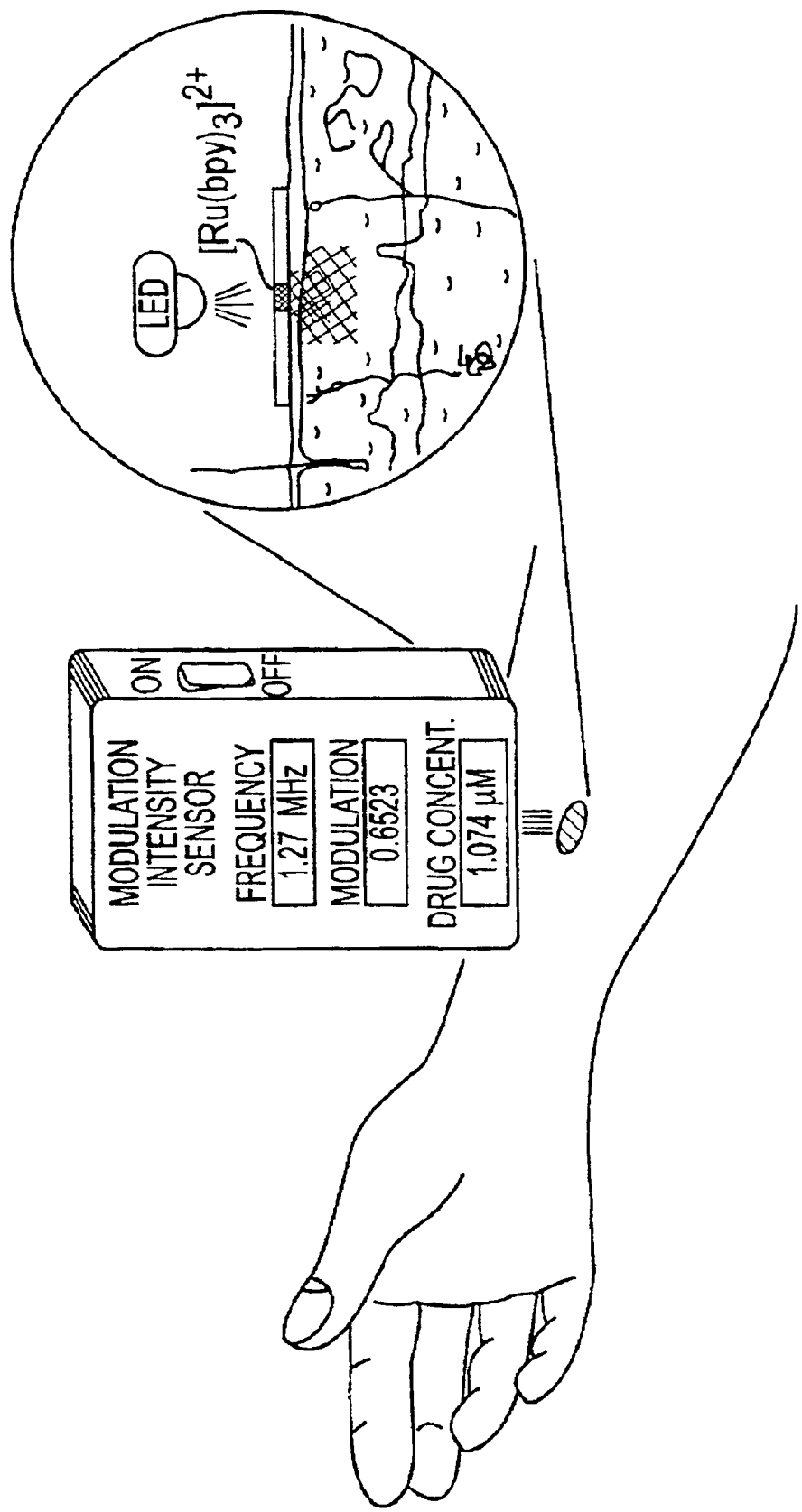
FIG. 1 is a schematic of a portable modulation intensity sensor.

Described here is a general method to perform sensing at low light modulation frequencies near 1 MHz using sensing fluorophores with ns lifetimes, without relying on a change in lifetime of the ns fluorophore. The basic idea is to use a mixture of the ns fluorophore with a fluorophore which displays a long lifetime near 1 µs. For such a mixture the modulation of the emission at intermediate frequencies becomes equivalent to the fraction of the total emission due to the short lifetime ns fluorophore. This occurs because the emission from the µs fluorophore is demodulated, and that of the ns fluorophore is near unity. This methods allows sensing based on modulation from about 1 to 10 MHz. Additionally, the ns sensing fluorophore does not need to display a change in lifetime. A simple change in intensity in response to the analyte is adequate for a low frequency modulation sensor.

The feasibility of this sensing scheme was demonstrated to be practical in several systems. First, the method was validated using a simple mixture of ns and µs fluorophores. We then devised assays for pH, and calcium. We note that this method is generic, and can be applied to any analyte for which an intensity-based sensor is available.

Abbreviations used in this disclosure are: PVA—polyvinyl alcohol; bpy—2,2'-bipyridyl; 6-CF—6-carboxyfluorescein; FD—frequency domain; BCECF is 2',7'-bis(2-carboxyethyl)-5(and 6)-carboxyfluorescein; [Ru(bpy)$_2$(dcbpy)]$^{2+}$ is Bis(2,2'-bipyridine)(2,2'-bipyridine-4,4'-dicarboxylic acid)ruthenium(II); C. is carboxy; SNAFL is seminaphtofluorescein; and SNARF is seminaphtorhodaflour.

The methods described herein allow measurement of many analytes. These include, but are not limited to, H$^+$, pH, Na$^+$, K$^+$, Li$^+$, Mg$^{2+}$, Ca$^{2+}$, Cl$^-$, HCO$_3^-$; CO$_2$, O$_2$, glucose, lactate, antigens and drugs. A large number of different fluorophores can be used as the sensing fluorophores and as the long lifetime fluorophores. Analyte sensing fluorophores include, but are not limited to, Quin-2, Fura-2, Indo-1, Calcium Green, Calcium Orange, Calcium Crimson and Benzoxazine-crown which are useful as Ca$^{2+}$ probes; Mag-Quin-2, Magnesium Green, and Benzoxazine-crown as Mg$^{2-}$ probes; PBFI as a K$^+$ probe, Sodium Green as a Na$^+$ probe, and SNAFL-1, C. SNAFL-1, C. SNAFL-2, C. SNARF-1, C. SNARF-2, C. SNARF-6, C. SNARF-X, BCECF, and Resorufin Acetate as pH probes. Probes for Cl$^-$ include 6-methoxy-N-ethylquinolinium chloride; N6-methoxyquinolyl)acetoethyl ester; 6-methoxy-N-ethylquinolinium chloride; 6-methoxy-N-(3-trimethylammoniumpropyl)quinolinium dibromide; 6methoxy-N-(3-trimethylammoniumpropyl) phenanthrindium dibromide; and 6methoxy-N-(4-aminoalkyl)quinolinium bromide hydrochloride. The above fluorophores are described in Szmacinski and Lakowicz 1994a. Other chloride probes include 6-methoxy-N-(3-sulfoproxyl)quinolinium; N-sulfopropylacridinium; N,N-dimethyl-9,9'-bisacridinium nitrate; N-methylacridinium-9-carboxamides; and N-methylacridinium-9-methylcarboxylate. Additional probes useful for measuring pH include 8-hydroxypyrene-1,3,6-trisulfonate; [Ru(4,4'-diethylaminomethyl-2,2'-bipyridine)(2,2'-bipyridine)$_2$]$^{2+}$; Oregon Green, DM-NERF and Cl-NERF. Additional fluorophores sensitive to Mg$^{2+}$ include Mag-Quin-1; Mag-Fura-2; Mag-Fura-5, Mag-Indo-1; Mag-Fura-Red; and Mg Orange. Additional fluorophores sensitive to Na$^+$ include sodium-binding benzofuran isophthalate and sodium-binding benzofuran oxazole. Additional fluorophores sensitive to K$^+$ include CD222. Additional fluorophores sensitive to Ca$^{2+}$ include Fura Red; BTC (coumarin benzothiazole-based indicator); Fluo-3; Ca Green-2; Ca Green-5N; Ca Orange-SN; Oregon Green - BAPTA-1, BAPTA-2 and BAPTA-5N. These additional analyte sensitive fluorophores are discussed in Lakowicz, 1999.

Fluorophores which are not sensitive to the analyte being tested but are used in conjunction with the analyte sensitive fluorophores include, but are not limited to, the compounds shown in FIGS. 20A–L.

In measuring analytes such as glucose, lactate, drugs or antigens, it is desirable to use a binding agent labeled with a fluorophore such that the binding agent binds specifically to the analyte. For example, a glucose-binding protein, a glucose-galactose binding protein, or concanavalin A can be used in a method to measure glucose. A lactate binding protein can be used for measurement of lactate. Antibodies or antibody fragments can be used to measure drugs or antigens. Other binding agents known to those of skill in the art can also be used.

While the use of lifetime measurements solves many problems associated with non-invasive sensing, it is still desirable to develop methods which would allow quantitative intensity measurements through skin and in the presence of extensive scattering. Described here is a simple method to measure fluorescence intensities in scattering media. Fluorescence is defined as meaning fluorescence, phosphorescence, luminescence or mixed-state emissions. This method is based on measurement of the modulation of the emission when the sample is excited with amplitude modulated light. In this method, the emission of the scattering sample is observed along with the emission of a long lifetime reference fluorophore. The reference fluorophore need not be within the sample, but can be on the surface outside the sample. This geometry is useful for sensing devices in which the long lifetime reference is held against the skin. The light modulation and measurement frequency is chosen so that the emission from the long-lifetime reference is completely demodulated. Under these conditions, the intensity of the fluorophore of interest with a ns decay time is given by the modulation of the total signal. This method can be applied to any sample which displays changes in intensity, or any sensing fluorophore which shows intensity changes due to its response to an analyte of interest. One can imagine this method being used with a hand-held instrument for point-of-care transdermal measurements. The method can be performed on a variety of systems or samples, including in vivo, blood plasma, whole blood, saliva, any body fluid, tissue culture, a sample from an aquarium, etc. Furthermore, the method may be used to monitor a bioprocessing reaction, industrially, in process control, as part of an analytical chemistry process, etc. The incident light can be produced by, but is not limited to, a laser, a light emitting diode (LED) or an electroluminescent light source (ELL).

Intensity decays were measured using the frequency-domain method. This method and procedure for data analysis have been described in detail (Lakowicz and Gryczynski, 1991; Lakowicz, in press; Lakowicz et al., 1984; Gratton et al., 1984; Lakowicz and Gryczynski, 1991). In this method one measures the phase ($\phi_\omega$) and modulation ($m_\omega$) of the emission for various values of the light modulation frequency ($\omega$, in radians/sec). A number of different models were used to analyze the FD data. Initially, the intensity decays were analyzed in terms of the multi-exponential model, $$I(t) = \sum_i \alpha_i \exp(-t/\tau_i) \tag{1}$$

where $\alpha_i$ are the pre-exponential factors and $\tau_i$ the decay times. The fractional steady state intensity disassociated with each decay time is given by $$f_i = \frac{\alpha_i \tau_i}{\sum_j \alpha_j \tau_j}. \tag{2}$$

Generally, $\Sigma\alpha_i$ and the $\Sigma f_i$ are constrained to be equal to unity.

For the present disclosure, it is instructive to consider the theory for a sample which displays two widely different decay times, the short ($\tau_S$) and long ($\tau_L$) decay times. For a mixture of fluorophores the phase and modulation can be calculated using $$N_\omega = \Sigma f_i m_i \sin \phi_i \tag{3}$$

$$D_\omega = \Sigma f_i m_i \cos \phi_i \tag{4}$$

where $f_i$ is the fractional intensity, $\phi_i$ is the phase angle and $m_i$ is the modulation of each fluorophore. The terms $N_\omega$ and $D_\omega$ are typically referred to as the sin and cosine transforms of the intensity decays (Lakowicz et al., 1984; Gratton et al., 1984). If each fluorophore displays a single exponential decay time $\tau$ then $$\tan \phi_\omega = \omega\tau \tag{5}$$

$$m_\omega = (1+\omega^2\tau^2)^{-1/2}. \tag{6}$$

For a multi-exponential decay the phase and modulation at any given frequency w are given by $$\tan \phi_\omega = N/D \tag{7}$$

$$m_\omega = (N^2+D^2)^{1/2}. \tag{8}$$

In the present study the samples display two widely different decay times, which we will refer to as the short ($\tau_S$) and long ($\tau_L$) decay times. In this case the values of N and D are given by $$N = f_S m_S \sin \phi_S + f_L m_L \sin \phi_L \tag{9}$$

$$D = f_S m_S \cos \phi_S + f_L m_L \cos \phi_L, \tag{10}$$

where we have dropped the subscript $\omega$ referring to the light modulation frequency. The total fractional intensity is normalized $f_S + f_L = 1.0$. If the two lifetimes are very different one can identify intermediate frequencies where the modulated emission of the short component is high is and that of the long lifetime component is low. Suppose the sample is examined at an intermediate modulation frequency such that the modulation of the short component is unity ($m_S = 1.0$) and the modulation of the long component is near zero ($m_L = 0.0$). In this case $$N = f_S \sin \phi_S \tag{11}$$

$$D = f_S \cos \phi_S \tag{12}$$

Using equation 8, and recalling the $\sin^2\theta + \cos^2\theta = 1.0$, one obtains $$m = f_S. \tag{13}$$

This is a useful result which indicates that the modulation of the emission is the fractional intensity of the short lifetime component. Hence, one can use the modulation of the emission to measure the fractional fluorescence intensity of the short lifetime fluorophore. In the present disclosure the short lifetime fluorophores were selected to display changes in intensity in response to the analyte. The long lifetime fluorophore is [Ru(bpy)$_3$]$^{2+}$, and is not sensitive to changes in pH or calcium over the investigated concentration ranges.

Measurements of nanosecond and subnanosecond lifetimes in scattering media can be affected by the time-dependent migration of photons due to the multiple scattering events. This topic has been described in detail (Hutchinson et al., 1995; Szmacinski and Kakowicz, 1994b). When a pulse of light enters the scattering media, the diffusely scattered light is delayed in time and the pulse is broadened. These effects can be described phenomenologically in terms of a time delay ($t_L$), a decay time for the light in the tissues ($t_D$) and a term describing the pulse broadening ($\Delta t$) (Szmacinski and Lakowicz, 1994b). For a fluorophore which displays a lifetime $\tau$ the phase and modulation measurement in scattering media is give by (Szmacinski and Lakowicz, 1994b), $$\phi^S_\omega = \arctan(\omega\tau) + \arctan(\omega t_D) + \omega t_L \quad (14)$$

$$m^S_\omega = (1+\omega^2\tau^2)^{-1/2}(1+\omega^2 t_D^2)^{-1/2} m_{\Delta t} \quad (15)$$

where $$m_{\Delta t} = (1+\omega^2\Delta t^2)^{-1/2} \quad (16)$$

Examination of Eqs. 14 and 15 indicate that the effects of the lifetime ($\tau$) and the photon decay time ($t_D$) are similar. Fortunately, the values of the decay time $t_D$ are modest for all but the shortest lifetimes. For instance, the value of $t_D$ for a position 4 mm deep in the 1% intralipid is about 140 ps (Szmacinski and Lakowicz, 1994b). Hence, for lifetimes 1 ns and longer, use of the values of $\phi^S_\omega$ and $m^S_\omega$ provides a good approximation ($\tau_{app}$) to the true lifetime ($\tau$)

$$\phi^S_\omega = \arctan(\omega\tau_{app}) + \omega t_L \quad (17)$$

$$m^S_\omega = (1+\omega^2\tau_{app}^2)^{-1/2} m_{\Delta t} \quad (18)$$

Some of the data were analyzed in terms of this model. Hence, we can expect an apparent lifetime for a fluorophore in scattering media to be 0.1 to 0.2 ns longer than in the absence of light scatter. We note the difference between the true and apparent lifetime depends on the method used to measure the phase and modulation of the excitation light. Importantly, the effects due to time-dependent photon migration occur mostly on the subnanosecond timescale and at frequencies above 100 MHz. Hence, it is not necessary to consider these effects for the low-frequency modulation measurements.

The parameters describing the intensity decays were obtained by non-linear least squares and minimization of $\chi_R^2$, $$\chi_R^2 = \frac{1}{\upsilon}\sum_\omega \left(\frac{\varphi_\omega - \varphi_{c\omega}}{\delta\phi}\right)^2 + \frac{1}{\upsilon}\sum_\omega \left(\frac{m_\omega - m_{L\omega}}{\delta\omega}\right)^2 \quad (19)$$

In this expression, the subscript c indicates calculated values for assumed parameter values. The terms $\delta\phi$ and $\delta m$ are the uncertainties in the phase and modulation data, respectively, and $\nu$ is the number of degrees of freedom. For the present measurements, we used of $\delta\phi=0.3°$ and $\delta m=0.007$.

The present invention is further detailed in the following Examples, which are offered by way of illustration and are not intended to limit the invention in any manner. Standard techniques well known in the art or the techniques specifically described below are utilized.

EXAMPLE 1

Materials and Methods

The following reagent grade chemicals were obtained from commercial sources and used as received: Ru(bpy)$_3$ Cl$_2$6H$_2$O (Aldrich), 6-carboxyfluorescein (6-CF) (Eastman/Kodak), Fluo-3 pentapotassium salt (Molecular Probes), calcium calibration buffer kit #2 (C-3009, Molecular Probes), and TRIS (Sigma). Disodium fluorescein was from Exciton, Inc. Intralipid (20%) was obtained from Kabi Vitrum, Inc. and diluted 40-fold to 0.5%. Water was deionized with a Milli-Q purification system. Solutions ranging from pH 5.0 to 9.1 were prepared in 50 mM TRIS buffer for the 6-carboxyfluorescein studies. Experiments using the Ca$^{2+}$ indicator Fluo-3 were performed solely in plastic media to prevent uptake of Ca$^{2+}$ from glass surfaces. All solutions were prepared in plastic vials from the calcium calibration buffer. Luminescence measurements were performed in polystyrene plastic cuvettes. In one experiment Ru(bpy)$_3$Cl$_2$ was in a polyvinyl alcohol film on the outside of the cuvette. In all other studies a small aliquot of aqueous Ru(bpy)$_3$Cl$_2$6H$_2$O was added to solutions containing the nanosecond fluorophore (6-carboxyfluorescein or Fluo-3) with analyte. We used these two different configurations to demonstrate the versatility of this approach to sensing. Typically, the steady-state emission intensity of Ru(bpy)$_3$ Cl$_2$6H$_2$O contributed about 20–30% of the total sample intensity at the highest pH (6-carboxyfluorescein) or at the highest Ca$^{2+}$ concentration (Fluo-3). All samples were optically dilute (<0.1 OD) at 488 nm.

Figure 2:
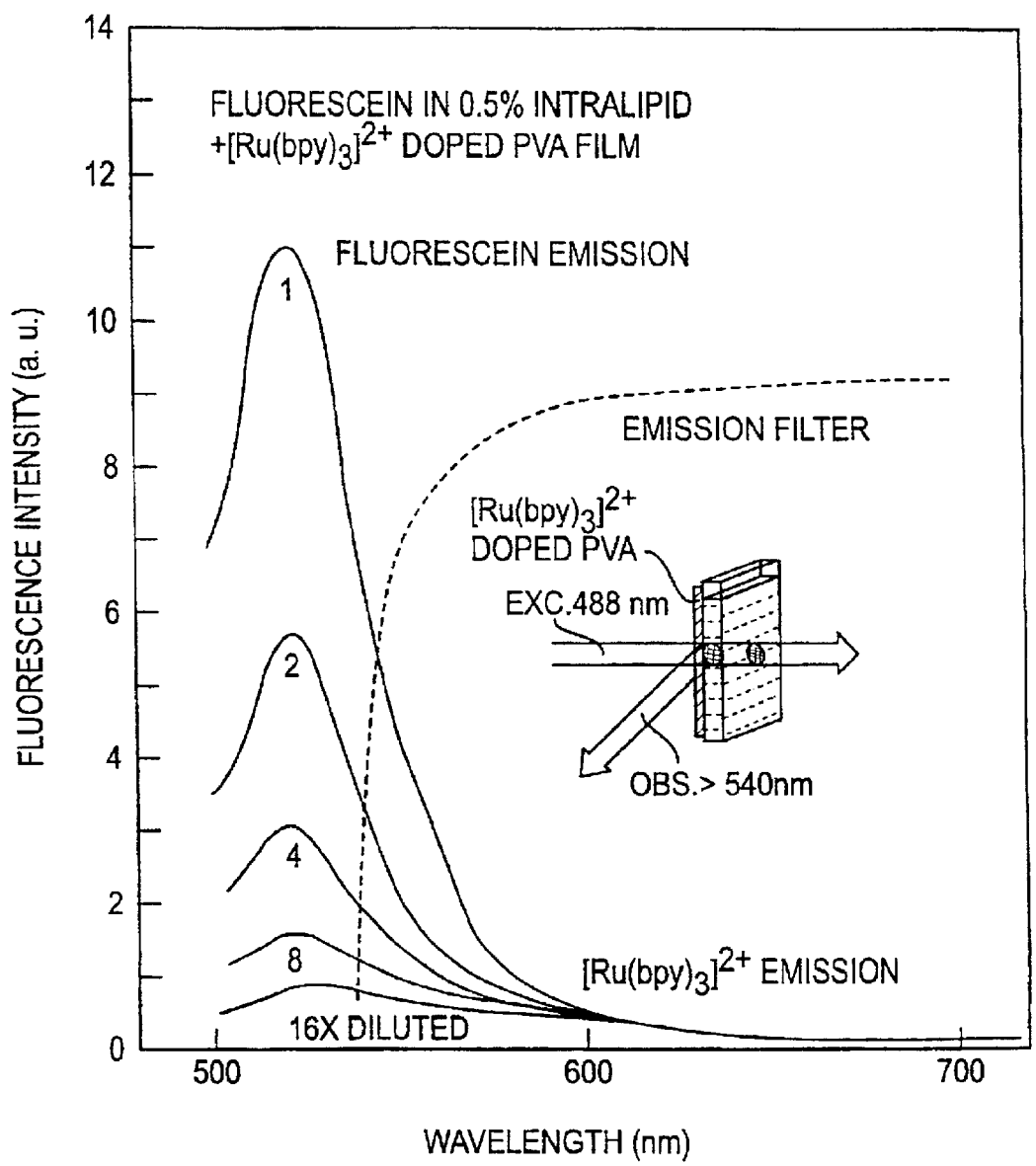
FIG. 2 shows emission spectra of fluorescein in 0.5% intralipid. Excitation at 488 nm. The dashed line shows the transmission curve of the emission filter. Emission for [Ru(bpy)$_3$]$^{2+}$ in the PVA film is responsible for the weak emission near 600 nm.

Experiments were performed using the geometry shown as an insert in FIG. 2. The intralipid sample was contained in a 2 mm×10 mm cuvette, with the 488 nm excitation incident on the wider 10 nm surface. This surface of the cuvette was covered with a film of polyvinyl alcohol (PVA) which contained the long-lifetime fluorophore Ru(bpy)$_3$Cl$_2$. The emission was observed from the 2 mm side through a filter which transmitted part of the fluorescein emission and most of the [Ru(bpy)$_3$]$^{2+}$ emission. The transmission curve of this filter is shown as a dashed line in FIG. 2.

EXAMPLE 2

Instrumentation

UV-Vis absorption spectra were measured on a Hewlett Packard 8453 diode array spectrophotometer with ±1 nm resolution. Uncorrected steady-state emission spectra were obtained on a SLM AB-2 fluorimeter under magic angle polarization conditions. Time-resolved luminescence decays were measured in the frequency domain (ISS, Koala) using an air cooled cw-Ar$^+$ laser (Omnichrome, 543-AP) operating at 488.0 nm (80 mW) as the excitation source. The 488 nm output was amplitude modulated using an electro-optic modulator, which provided modulated excitation from 300 kHz to 150 MHz. This frequency-domain instrument was comparable to those described previously (Gratton and Limkeman, 1983; Lakowicz and Maliwal, 1985).

The laser was passed through a Pockels cell which provided modulated light from 300 kHz to 150 MHz Two different PTS frequency synthesizers (PTS-500) were used to modulate the Pockels cell and detection system. The output of the PTS synthesizer driving the Pockels cell was amplified by an ENI 25 W linear RF amplifier (325 LA, 250 kHz–150 MHz) prior to Pockels cell input. The other PTS synthesizer output was directed into an ENI 3 W linear RF amplifier (403 LA, 150 kHz–300 MHz) for proper modulation of the detection system. The emission was observed as usual at 90° to the excitation through an appropriate combination of long-pass filters which eliminated scattered light at the excitation wavelength. We used this experimental configuration because it was available in this laboratory. In the actual use of modulation sensing we expect the light source will be an intensity modulated LED or some other solid state light source.

The intensity decays were analyzed in terms of the multi-exponential model, $$I(t) = \sum_i \alpha_i \exp(-t/\tau_i) \quad (1)$$

where $\alpha_i$ are the pre-exponential factors and $\tau_i$ the decay times. The fractional steady state intensity dissociated with each decay time is given by $$f_1 = \frac{\alpha_i \tau_i}{\sum_j \alpha_j \tau_j}. \quad (2)$$

Generally, $\Sigma \alpha_i$ and the $\Sigma f_i$ are constrained to be equal to unity. Rhodamine B in water with a lifetime of 1.68 ns was used as a lifetime reference in the frequency-domain experiments (Gryczynski et al., 1997). Luminescence decays were analyzed by non-linear least squares procedures described previously (Lakowicz et al., 1984, Gratton et al., 1984). Global analysis of frequency-domain emission decay data was performed with programs developed at the Center for Fluorescence Spectroscopy, In the global analysis, the lifetimes were the global parameters and the amplitudes were fitted as non-global parameters. This means that the lifetimes were fitted parameters, but were constrained to be the same values at all analyte concentrations or all pH values for 6-CF. The amplitudes were also fitted parameters, but were allowed to vary at each analyte concentration or pH value.

EXAMPLE 3

Model Sensors with Varying Fluorescein Concentration

Figure 3A:
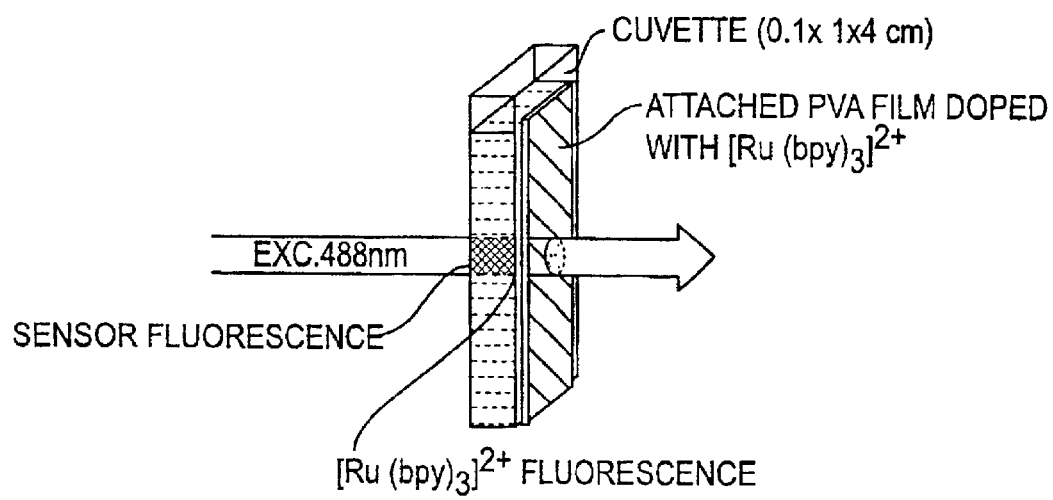
FIGS. 3A and 3B are schematics of sensors with a ns fluorophore and [Ru(bpy)$_3$]$^{2+}$.
Figure 4:
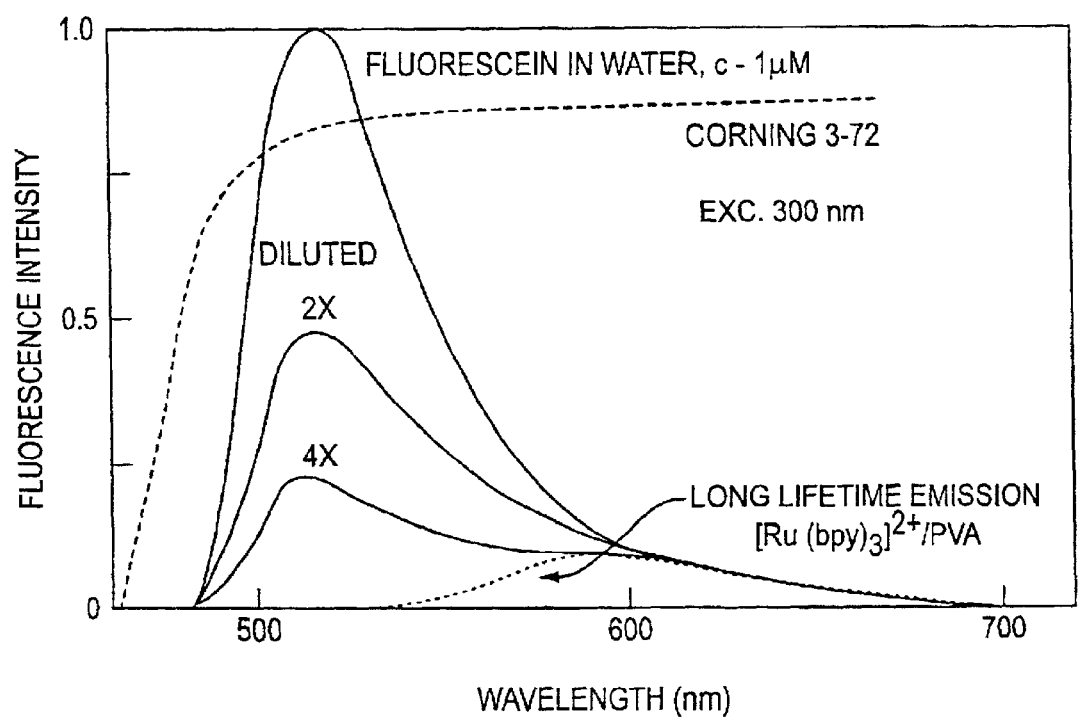
FIG. 4 shows emission spectra of the model sensor containing fluorescein in the internal aqueous phase and [Ru(bpy)$_3$]$^{2+}$ in an external PVA film.

To test the principal of modulation sensing we performed frequency domain measurements for a sample which displayed emission from both $[Ru(bpy)_3]^{2+}$ and fluorescein. In this case the two fluorophores were physically separated, which is a useful configuration if the sensing fluorophore can interact with the reference fluorophore. The long lifetime fluorophore $[Ru(bpy)_3]^{2+}$ was dissolved in melted polyvinyl alcohol (PVA) which was painted on the outer surface of the cuvette (FIG. 3A). Aqueous solutions of fluorescein were placed within the cuvette. This model assay was excited at 488 nm with an argon ion laser. Emission spectra of this sample are shown in FIG. 4. The fluorescein dominates the emission spectra with a maximum near 510 nm. The emission from $[Ru(bpy)_3]^{2+}$ occurs at longer wavelengths with an emission maxima near 590 nm.

For FD measurements the emission was observed through a Corning 3-72 filter, which transmitted the emission from both 6-CF and $[Ru(bpy)_3]^{2+}$ (FIG. 4). The relative proportion of the two emissions were varied by dilution of the fluorescein within the cuvette (FIG. 4). The concentration and emission intensity of $[Ru(bpy)_3]^{2+}$ remained the same as the fluorescein was diluted.

Figure 5:
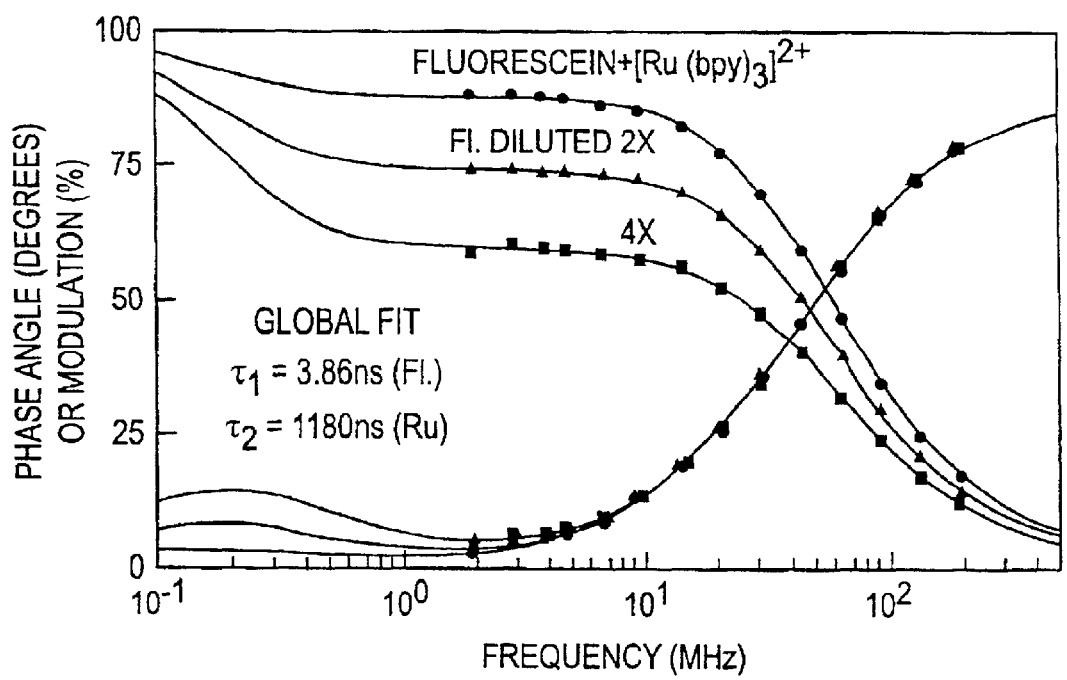
FIG. 5 shows the frequency-domain intensity decay of the fluorescein-[Ru(bpy)$_3$]$^{2+}$ model sensor.

FIG. 5 shows the frequency-domain intensity decays of this model assay. The emission is already demodulated below 1.0 for the lowest measurement frequency near 1.8 MHz. This effect is due to the long decay time of $[Ru(bpy)_3]^{2+}$ in PVA. In separate measurements the decay time of $[Ru(bpy)_3]^{2+}$ in PVA was found to be 1180 ns. The modulation is nearly constant from 2 to 8 MHz. This occurs because the modulation of $[Ru(bpy)_3]^{2+}$ is near zero, and that of fluorescein with a lifetime of 2.85 ns is near 1.0. In this low frequency range the modulation is expected to represent the fractional steady state intensity of the short lifetime emission (eq. 13). Comparison of FIGS. 4 and 5 shows that the modulation values at intermediate frequencies are approximately equal to the intensity of fluorescein relative to that of $[Ru(bpy)_3]^{2+}$.

EXAMPLE 4

Low Frequency Modulation pH Sensor

We use the concept described above to create a pH assay based on the modulation at the intermediate frequencies. As a pH-sensitive fluorophore we selected 6-carboxyfluorescein (6-CF). Fluorescein and its derivatives have been widely used for pH sensing (Thomas et al., 1979; Babcock, 1983: Klonis et al., 1998). Fluorescein and its derivatives display a pH-dependent dissociation of the carboxyl group. The ionized form which exists at pH values above 7.5 is highly fluorescent, and the protonated low pH form is essentially non-fluorescent. For this reason fluorescein is not known to display a change in lifetime when this dissociation reaction occurs.

Figure 3B:
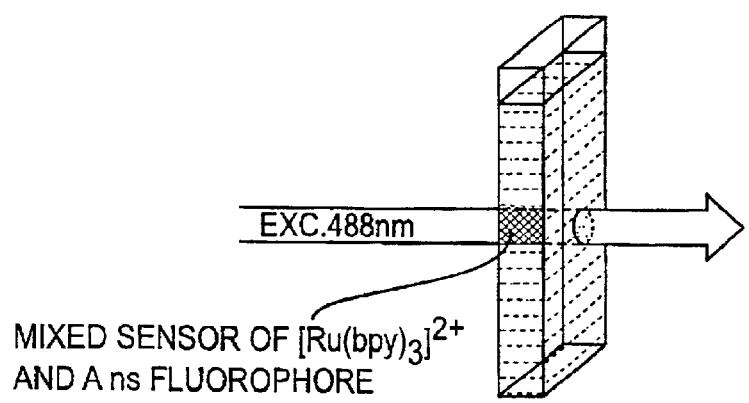
Figure 6:
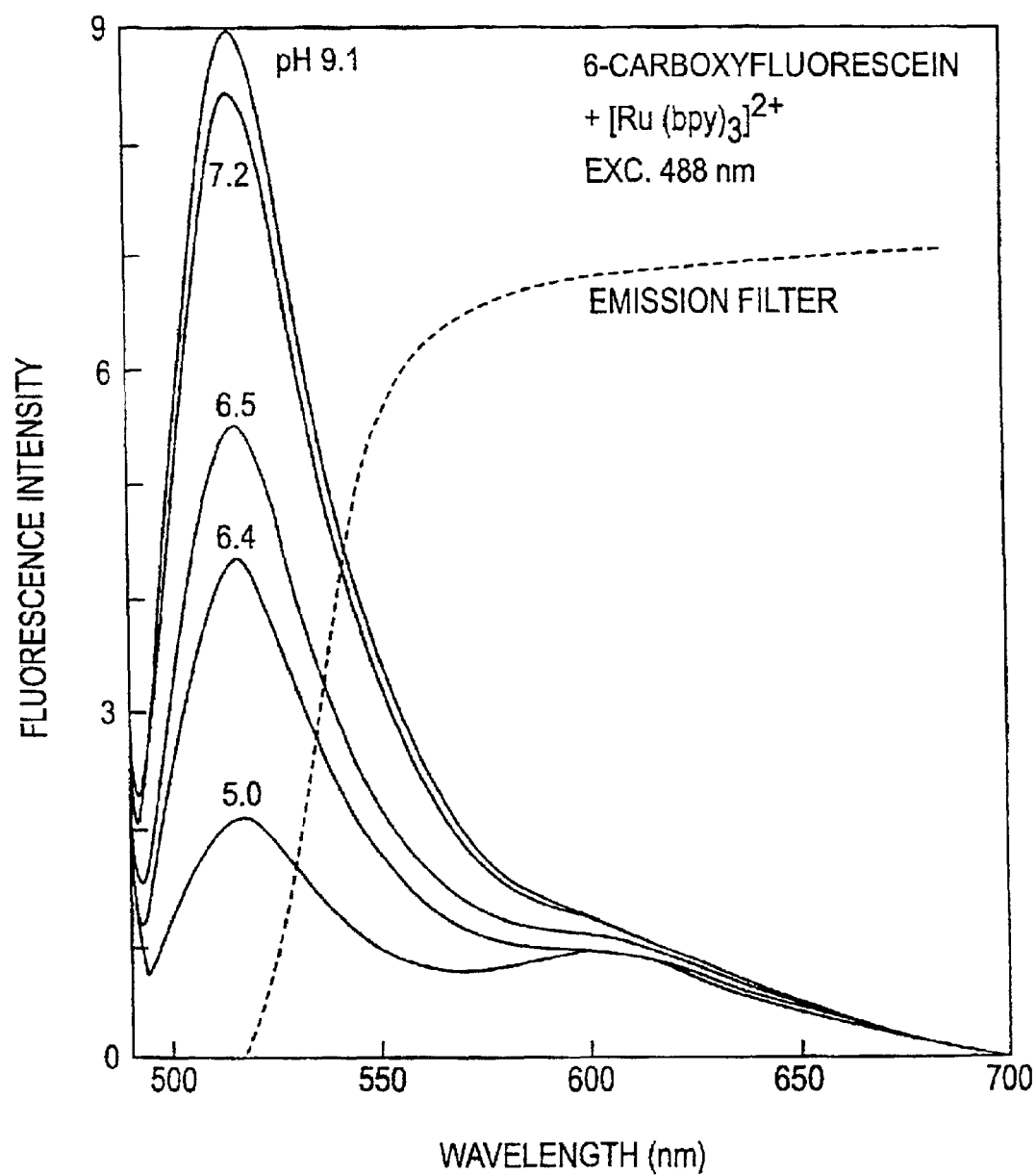
FIG. 6 shows emission spectra of a pH sensor based on a mixture of 6-carboxyfluorescein (6-CF) and [Ru(bpy)$_3$]$^{2+}$.

For the modulation pH assay the 6-CF and $[Ru(bpy)_3]^{2+}$ were both dissolved in the aqueous phase (FIG. 3B). We did not use the external PVA film. Emission spectra of this mixture shows that the 6-CF emission is strongly affected by pH, while the intensity of the long lifetime $[Ru(bpy)_3]^{2+}$ is essentially the same at all pH values (FIG. 6). The emission filter was selected to transmit all the $[Ru(bpy)_3]^{2+}$ emission and part of the 6-CF emission. In this way one can modify the fractional intensity from each fluorophore without changing the actual concentrations.

Figure 7A:
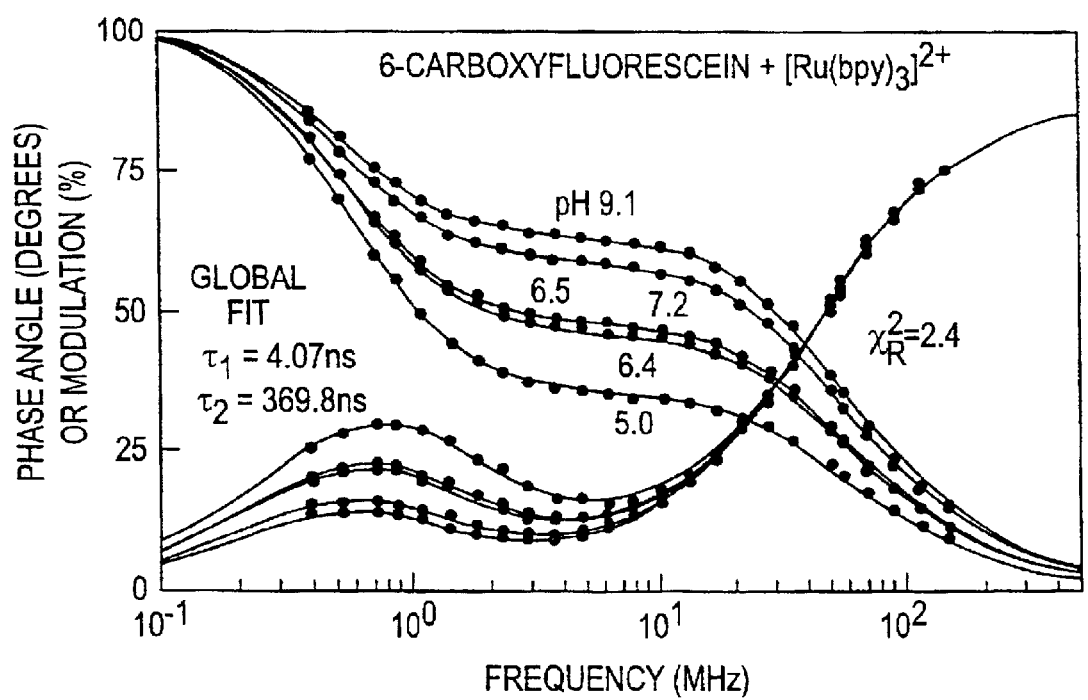
FIG. 7A shows the frequency response of the pH sensor.

Frequency-domain intensity decay data for the mixture of 6-CF and $[Ru(bpy)^3]^{2+}$ are shown in FIG. 7A. As expected based on the lifetimes of 6-CF (4.07 ns) and $[Ru(bpy)_3]^{2+}$ (370 ns) there is a region of constant modulation from 2 to 10 MHz. In this region the modulation of the emission increases due to the higher intensity of 6-CF at high pH. The frequency data were analyzed using the multi-exponential model (eq. 1). At all pH values the frequency responses could be fit to two decay times of 4.0 and 370 ns, as can be seen from the global analysis in Table I. As the pH value increases the fractional steady state intensity of the short component ($f_1$) also increases. For mixtures with such different lifetimes it is preferable to use the $f_1$ values, rather than the pre-exponential factors. The value of $\alpha_1$ is over 0.98 at all pH values.

TABLE I

Global Double-Exponential Analysis of the Intensity Decays of pH Sensor

| pH  | $\tau_1$ (ns) | $\tau_2$ (ns) | $\alpha_1$ | $\alpha_2$ | $f_1$ | $f_2$ | $\chi_R^2$ |
|-----|---------------|---------------|------------|------------|-------|-------|------------|
| 9.1 | 4.07          | 369.8         | 0.994      | 0.006      | 0.627 | 0.373 | 2.4        |
| 7.2 | "             | "             | 0.992      | 0.008      | 0.583 | 0.417 |            |
| 6.5 | "             | "             | 0.988      | 0.012      | 0.474 | 0.526 |            |
| 6.4 | "             | "             | 0.987      | 0.013      | 0.459 | 0.541 |            |
| 5.0 | "             | "             | 0.980      | 0.020      | 0.347 | 0.653 |            |

Figure 7B:
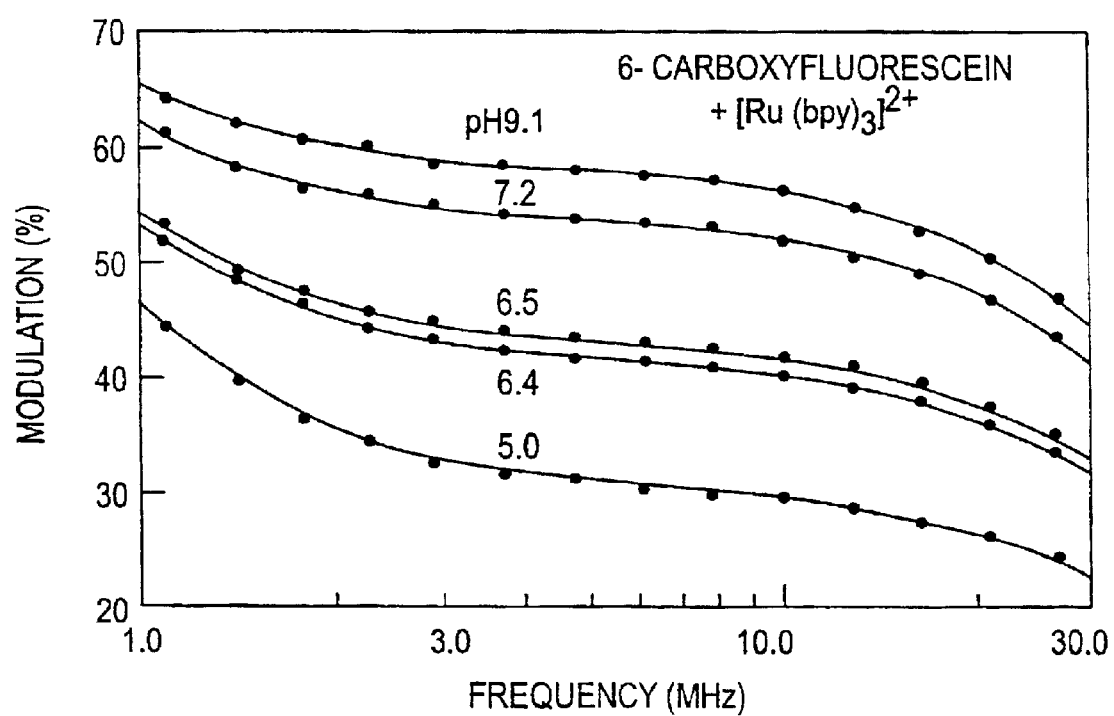
FIG. 7B shows the low frequency modulation of the pH sensor.
Figure 8:
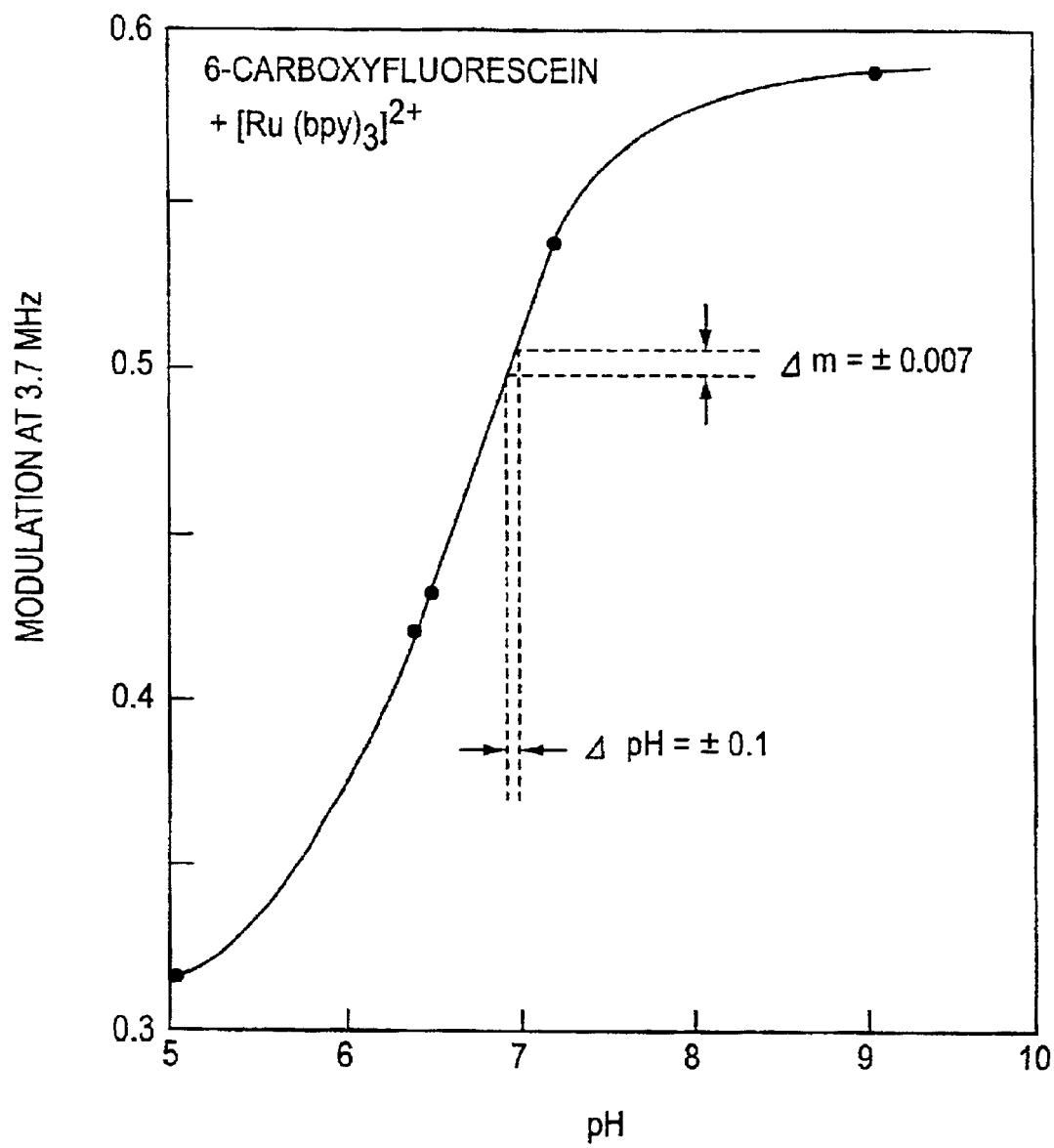
FIG. 8 shows a calculation curve of the pH sensor.

For clinical applications the pH values are typically accurate to ±0.02 or better (Mahutte et al., 1994a; Mahutte et al., 1994b; Shapiro et al., 1993; Mahutte, 1994). The present sensor was found to be sensitive to changes in pH of ±0.1, as can be seen in the modulation data on an expanded scale (FIG. 7B). For instance, pH values of 6.4 and 6.5 are easily distinguishable. Such data can be used to prepare a calibration curve for pH based on the modulation at 3.7 MHz (FIG. 5). Modulation measurements are readily accurate to ±0.007, which results in a pH accuracy of ±0.1 (FIG. 8). These results were obtained without optimizing the assay based on the relative intensities of the two species, and the overall change in intensity of the pH-sensitive fluorophore. Inclusion of measurements of the phase angle and modulation at more than one frequency will improve the pH accuracy.

EXAMPLE 5

A Modulation Sensor for Calcium

Calcium is known to be an intracellular messenger. Measurements of calcium concentrations have been the subject of numerous publications (Nuccitelli, 1994; Grynkiewicz et al., 1985). Calcium can be measured using intensity-ratiometric probes (Tsien et al., 1985; Kao, 1994; Tsien, 1989; Akkaya and Lakowicz, 1993) or using lifetime-based sensing (Lakowicz et al., 1992a; Hirschfield et al., 1993; Miyoshi et al., 1991; Lakowicz et al., 1992b; Lakowicz and Szmacinski. 1992). However, some calcium probes do not display spectral shifts upon binding calcium, and some probes do not display changes in lifetime. One such calcium probe is Fluo-3, which is highly fluorescent in the presence of bound calcium, but essentially non-fluorescent in the absence of calcium. Because the calcium-free probe does not fluoresce, the emission is due to only the calcium-bound form. For this reason only the calcium-bound form of Fluo-3 contributes to the lifetime, and thus Fluo-3 displays the same lifetime at all calcium concentrations.

Figure 9:
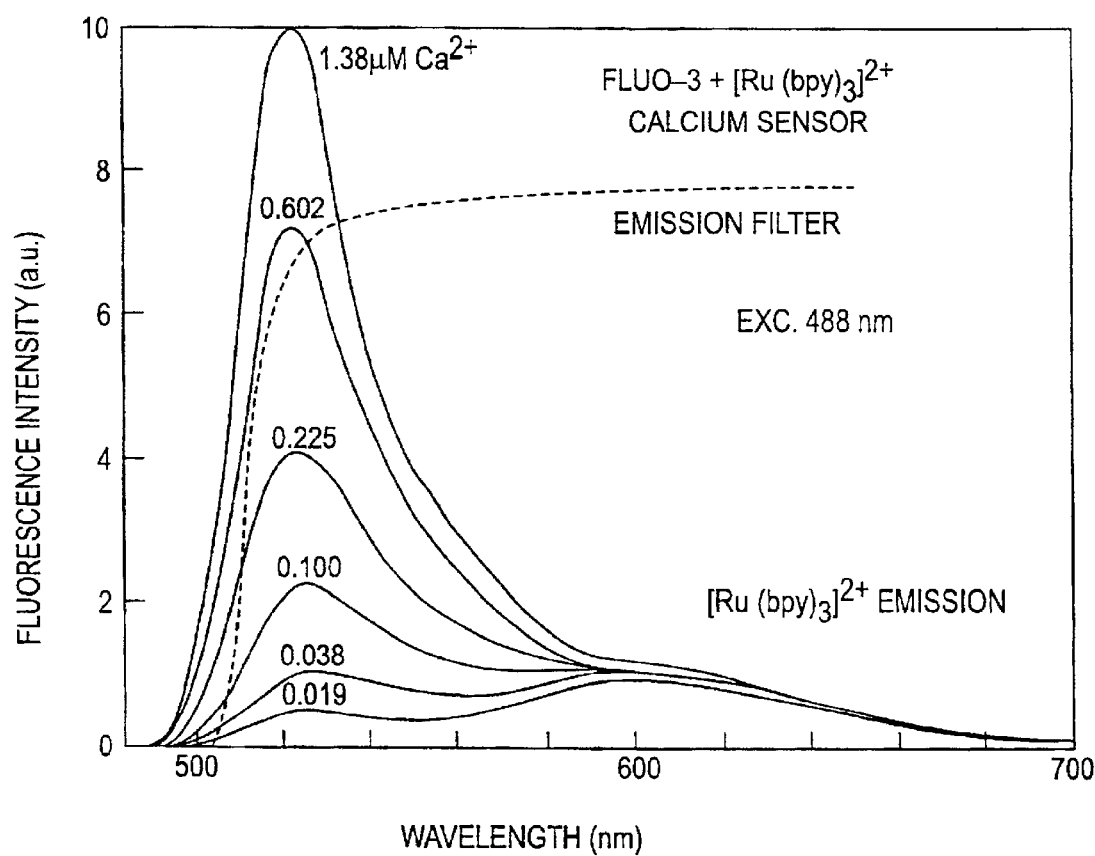
FIG. 9 shows emission spectra of a modulated calcium sensor based on Fluo-3 and [Ru(bpy)$_3$]$^{2+}$.
Figure 10:
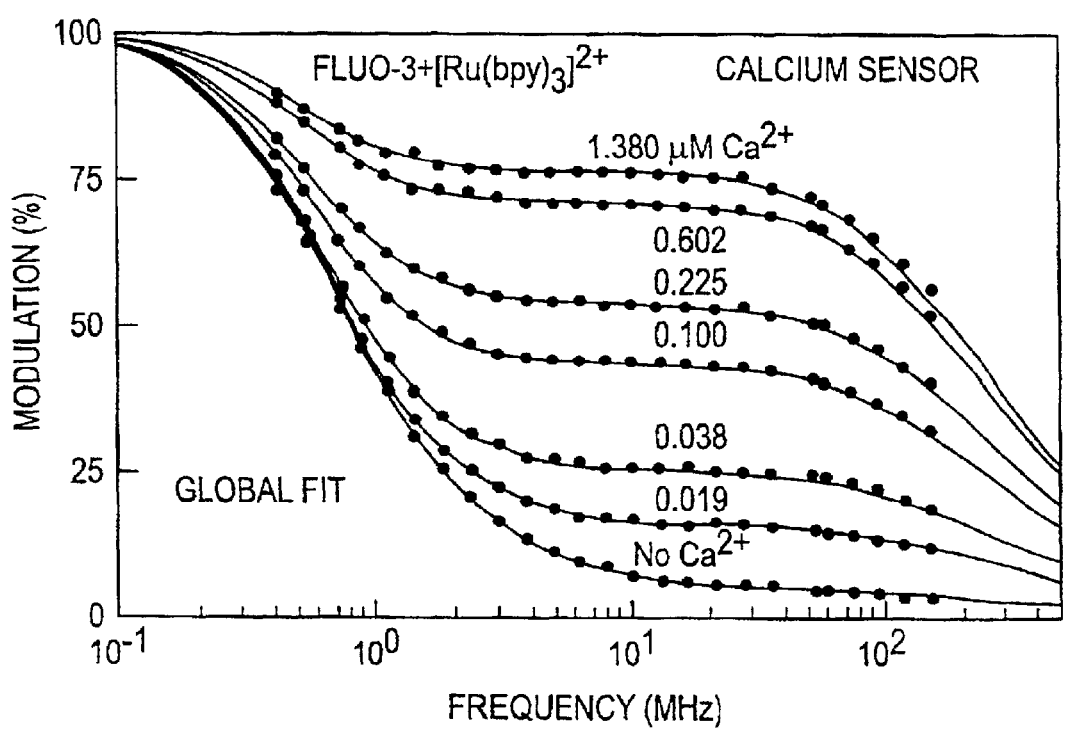
FIG. 10 shows a modulation frequency response of the calcium sensor.
Figure 11:
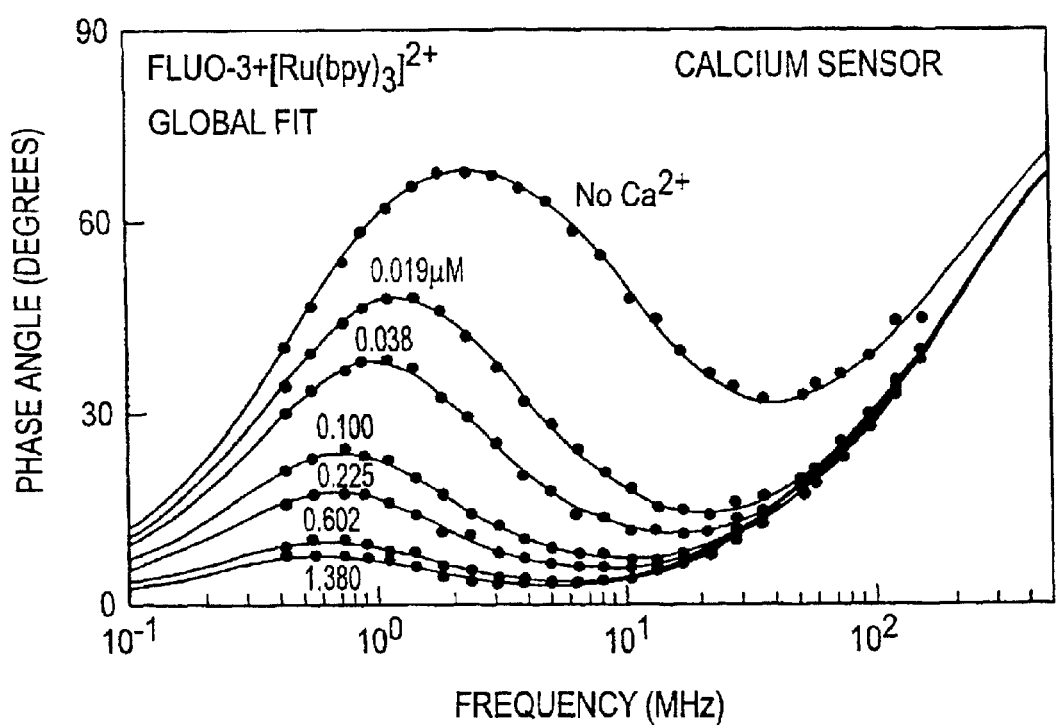
FIG. 11 shows phase angle frequency response of the calcium sensor.

While Fluo-3 cannot be used as wavelength-ratiometric or lifetime sensor for calcium, it can be used in our method of modulation sensing. This is shown in FIG. 9. In this assay both Fluo-3 and [Ru(bpy)$_3$]$^{2+}$ were contained within the cuvette. The emission of Fluo-3 at 510 nm increases dramatically in the presence of Ca$^{2+}$. The emission intensity of [Ru(bpy)$_3$]$^{2+}$ is not sensitive to calcium and is the same at all calcium concentrations. The frequency-dependent modulation of the Fluo-3 [Ru-(bpy)$_3$]$^{2+}$ mixture are shown in FIG. 10. As the calcium concentration increases so does the modulation from 2 to 30 MHz. We also examined the frequency-dependent phase angles (FIG. 11). The phase angles show a maximum near 1 MHz. The largest values near 1 MHz are seen in the absence of calcium, where the emission is dominated by the long lifetime Ru complex. As the calcium concentration increases the phase angles decrease to smaller values as the emission becomes dominated by the shorter lived emission from Fluo-3.

The modulation and phase angle frequency responses (FIGS. 10 and 11) were analyzed in terms of the multi-exponential model (eq. 1). Two decay times were needed to account for the emission from Fluo-3, 0.72 and 1.89 ns (Table II). The data at all calcium concentrations could be globally fit to the same three decay times, with the fractional intensities dependent on the calcium concentration.

Figure 12A:
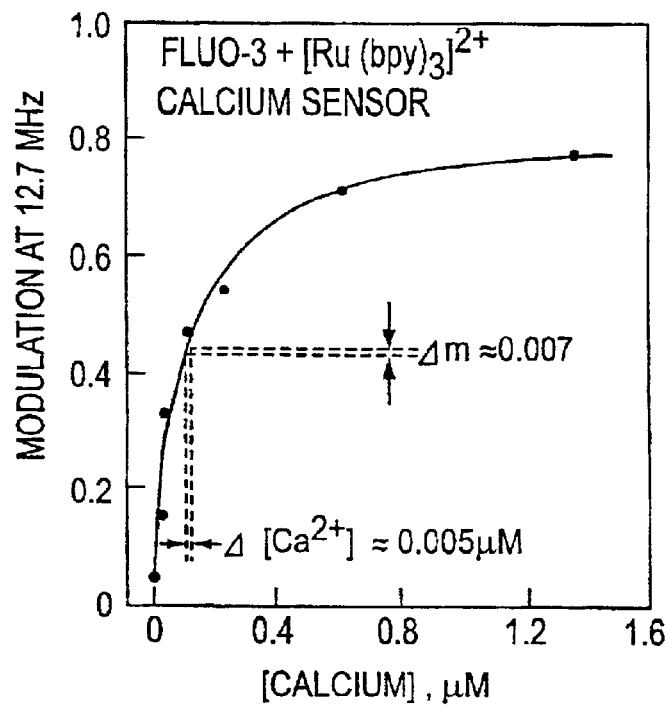
FIGS. 12A and 12B show phase and modulation calibration curves of the calcium sensor.
Figure 12B:
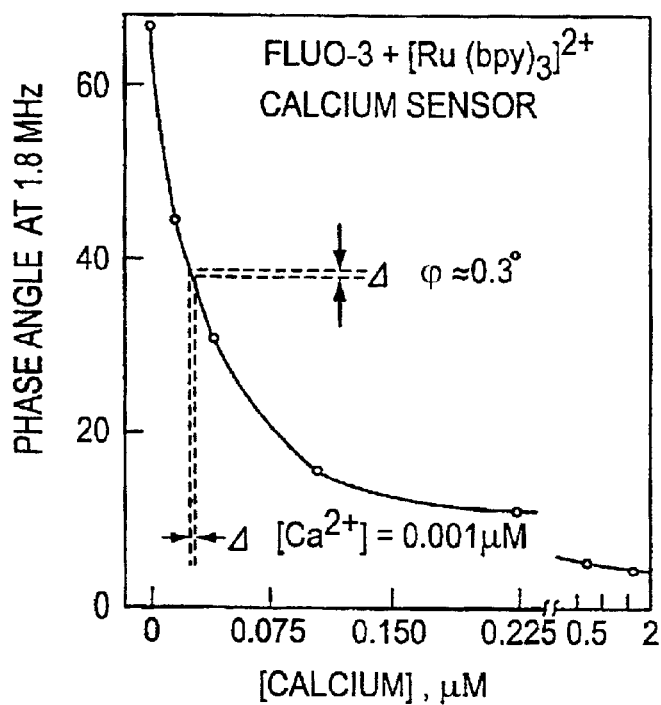

The data in FIGS. 10 and 11 were used to prepare calibration curves for calcium (FIGS. 12A and 12B). The modulation values 12.7 MHz show an apparent calcium dissociation constant ($K_D$) for Fluo-3 near 100 nM, which is lower than but comparable to the known dissociation constant near 400 mM (Minta et al., 1989; Kao et al., 1989; Harkins et al., 1993). Precise agreement between the thermodynamic $K_D$ value, and the apparent value from time-resolved data is not expected. Depending on the nature of the time-resolved measurements the apparent $K_D$ values can be larger or smaller than the true $K_D$ value (Szmacinski and Lakowicz, 1994a).

TABLE II

Global Intensity Decay Analysis of the Fluo-3 [Ru(bpy)$_3$]$^{2+}$ Calcium Sensor[a] Intensity Decay

| | $\tau_1$ = 0.72 ns | | $\tau_2$ = 1.89 ns | | $\tau_3$ = 359.8 ns | | |
|---|---|---|---|---|---|---|---|
| Ca$^{2+}$ (μM) | $\alpha_1$ | $f_1$ | $\alpha_2$ | $f_2$ | $\alpha_3$ | $f_3$ | $\chi_R^2$ |
| Ca$^{2+}$ Saturated | 0.733 | 0.415 | 0.266 | 0.397 | 0.001 | 0.188 | 2.2 |
| 1.38 | 0.857 | 0.531 | 0.143 | 0.233 | 0.001 | 0.235 | |
| 0.602 | 0.859 | 0.498 | 0.140 | 0.215 | 0.001 | 0.287 | |
| 0.225 | 0.875 | 0.392 | 0.123 | 0.145 | 0.002 | 0.463 | |
| 0.100 | 0.860 | 0.302 | 0.137 | 0.126 | 0.003 | 0.572 | |
| 0.038 | 0.861 | 0.171 | 0.132 | 0.069 | 0.007 | 0.760 | |
| 0.019 | 0.879 | 0.113 | 0.108 | 0.036 | 0.013 | 0.851 | |
| 0 | 0.692 | 0.020 | 0.240 | 0.018 | 0.068 | 0.962 | |

[a]In a calcium saturated solution, without [Ru(bpy)$_3$]$^{2-}$, Fluo-3 displayed a double exponential intensity decay with $\tau_1$ = 0.78 ns, $\tau_2$ = 1.92 ns, $\alpha_1$ = 0.768, $\alpha_3$ = 0.232, $f_1$ = 0.575 and $f_2$ = 0.425, $\chi_R^2$ = 0.9. The $\chi_R^2$ value for the single decay time fit for Fluo-3 alone was 18.2. In water [Ru(bpy)$_3$]$^{2+}$ displayed a single exponential decay of 370 ns.

The low frequency phase data were also used to prepare a calcium calibration curve (FIG. 12B). In this case the phase angles are sensitive to lower concentrations of calcium, with an apparent $K_D$ near 40 nM. This suggests the combined use of both the phase and modulation data to allow measurement of calcium over an extended range of concentrations, or to provide increased accuracy over a critical range of concentrations.

EXAMPLE 6

Fluorescein Concentrations in Intralipid

Quantitative intensity measurements in scattering media were tested using various concentrations of fluorescein in intralipid. Emission spectra are shown in FIG. 2. The maximum fluorescein concentration is 12 μm. The emission from this concentration of fluorescein can be easily seen even in 0.5% intralipid. As the fluorescein concentration is decreased, the intensity at 520 nm decreases. All the emission spectra shown in FIG. 2 were collected with the external PVA film containing [Ru(bpy)$_3$]$^{2+}$, which served as the reference fluorophore. The emission of [Ru(bpy)$_3$]$^{2+}$ occurs near 600 nm, and is visible on the long wavelength side of the fluorescein emission.

Figure 13A:
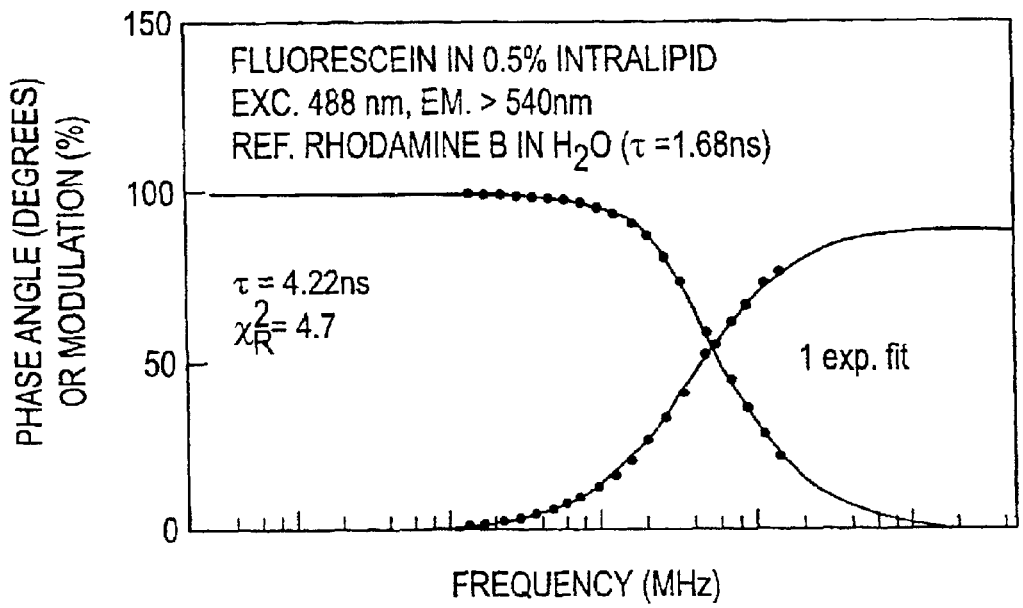
FIGS. 13A and 13B show frequency-domain intensity decay of the intralipid sample containing fluorescein. The cuvette did not have the external [Ru(bpy)$_3$]$^{2+}$-PVA film.
Figure 13B:
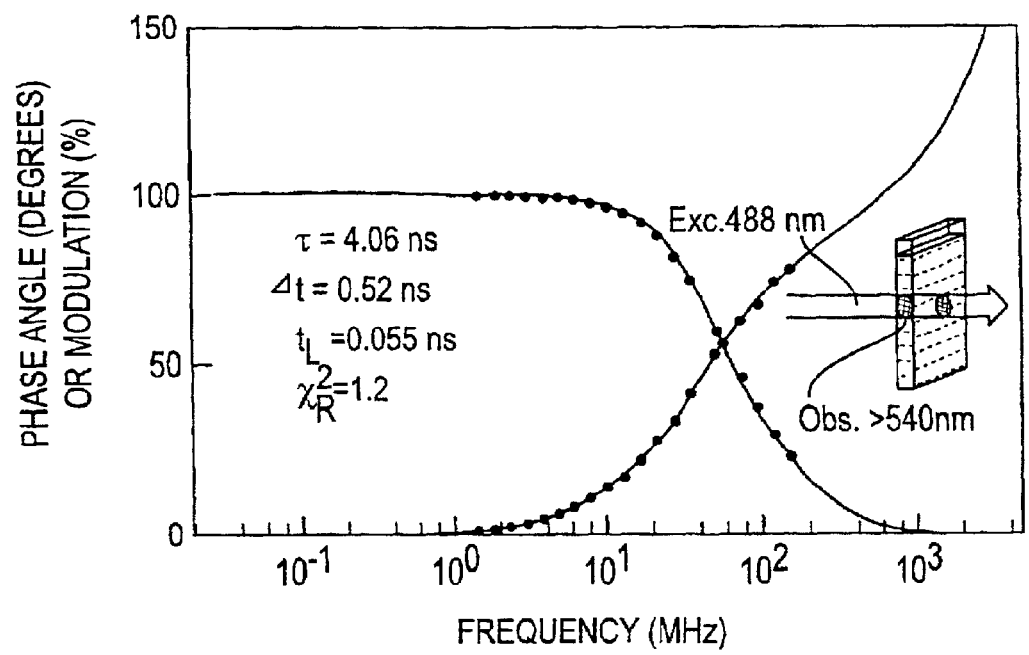

We examined the frequency response of fluorescein in 0.5% intralipid., without the long-lifetime reference (FIGS. 13A and 13B). The data could be fit reasonably well to a single decay time of 4.22 ns, but with a somewhat elevated value of $X_R^2$=4.7. The fit was improved using the models which included the effects of time-dependent photon migration (Eqs. 14–18). Use of this model resulted in a decrease of $X_R^2$ to 1.2. While the differences between the two fits in FIGS. 13A and 13B is not dramatic, our experience with the frequency domain measurements allows us to accept the model resulting in $X_R^2$=1.2. Importantly, the effects due to the scattering media are only significant at frequencies above 100 MHz. Hence. these effects can be neglected in the low-frequency modulation measurements which can be performed near 2 MHz.

Figure 14:
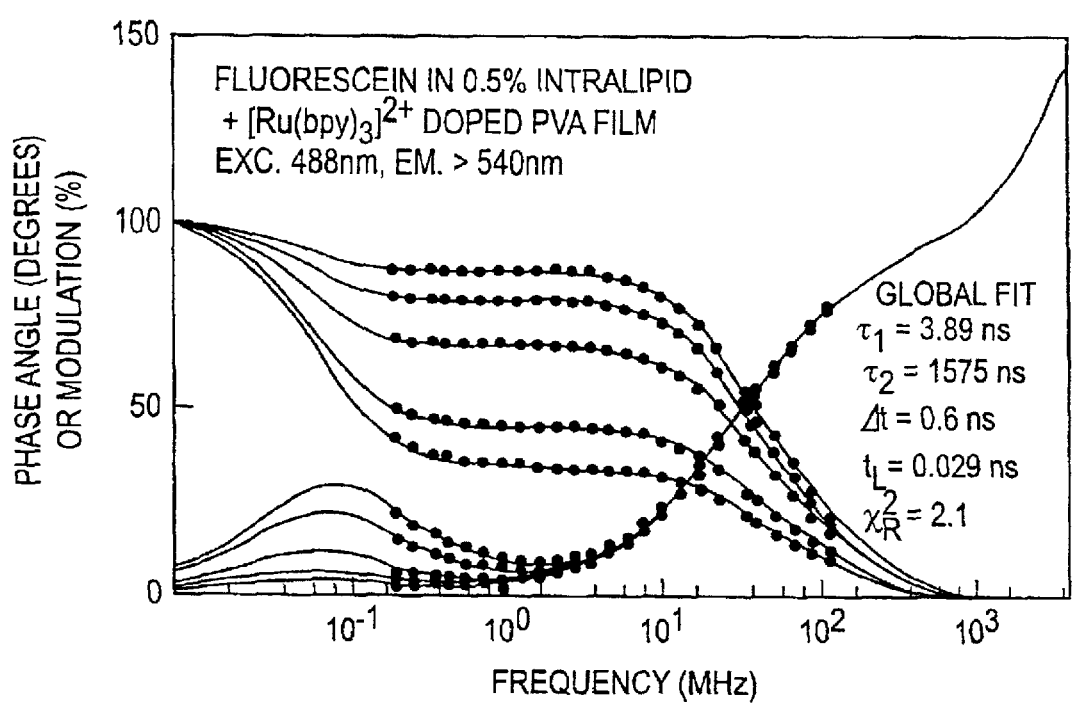
FIG. 14 shows a frequency response of the fluorescein-[Ru(bpy)$_3$]$^{2+}$ -intralipid sample shown in FIG. 1.
Figure 15:
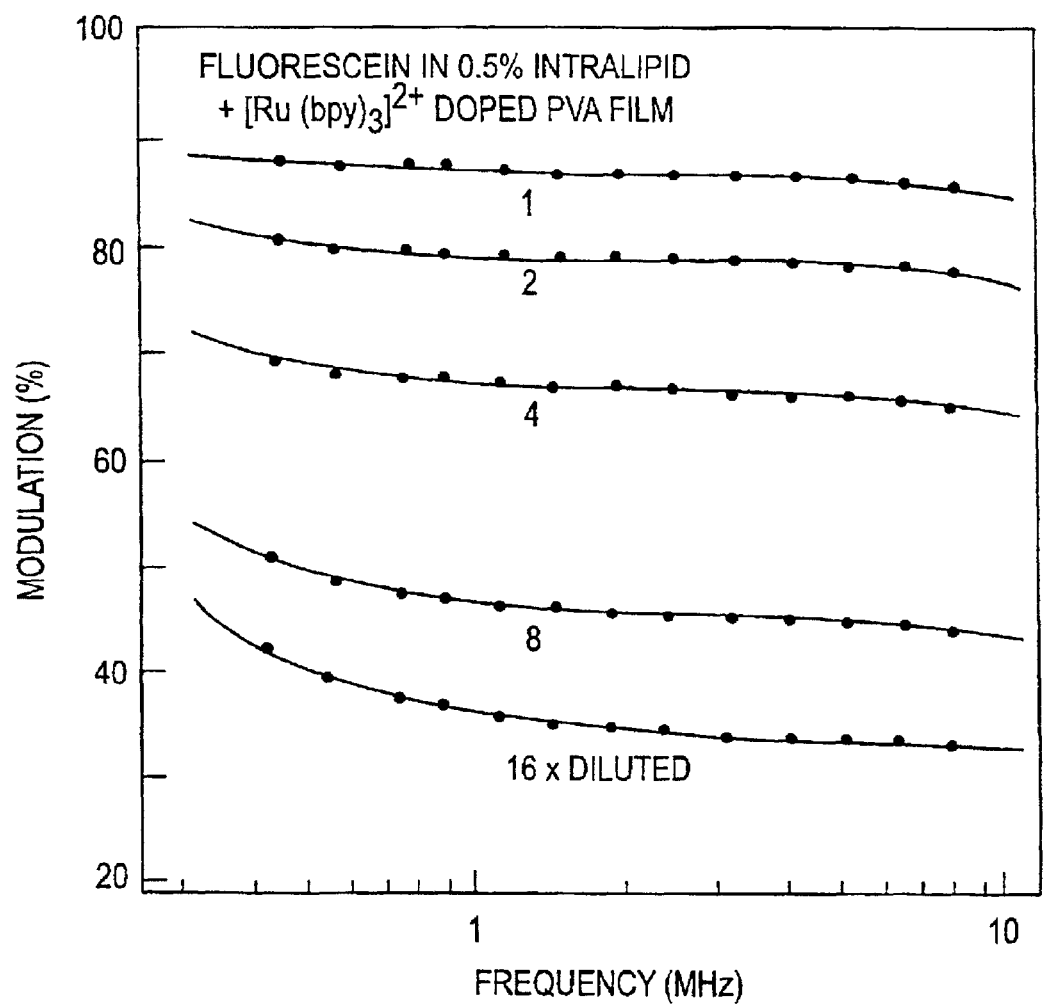
FIG. 15 shows low frequency modulation of the fluorescein-[Ru(bpy)$_3$]$^{2+}$ intralipid sample shown in FIG. 2.

We next used the configuration shown in FIG. 2 to test the concept of using the A modulation to measure the intensity. FIG. 14 shows frequency-domain measurements of the emission due to both fluorescein in intralipid and the long-lifetime reference. These data were analyzed globally using equations 14–18 (Table III). The long-lifetime of 1575 ns is essentially equivalent to that observed for $[Ru(bpy)_3]^{2+}$ alone in the PVA film. The lifetime of 3.89 ns is assigned to fluorescein. The modulation data over the range of frequencies is shown on an expanded scale in FIG. 15. One notices a region from 0.3 to 8 MHz over which the modulation is nearly independent of the light modulation frequency.

Figure 16:
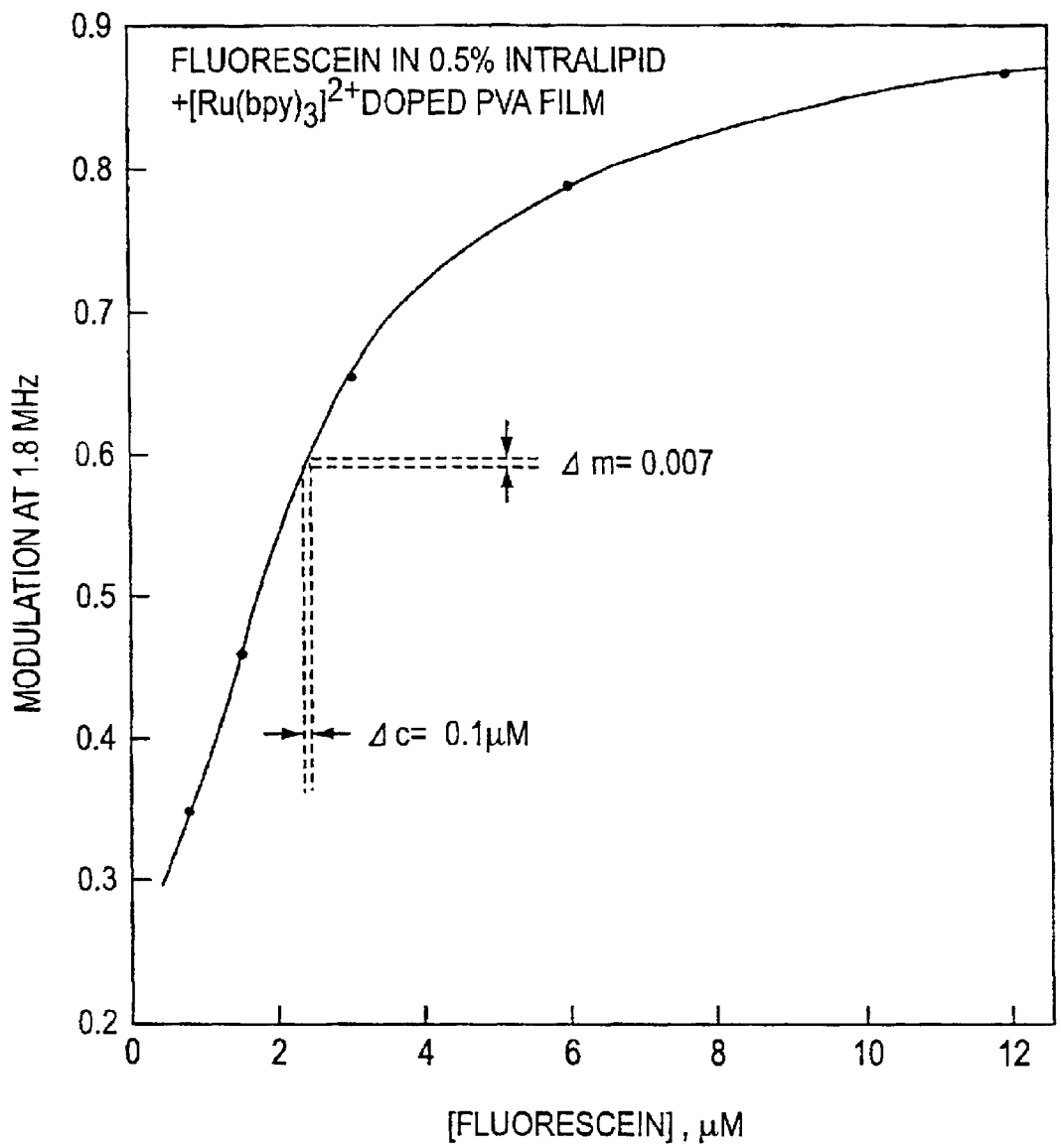
FIG. 16 shows modulation versus fluorescein concentration.

The modulation data at 1.8 MHz were used to prepare a calibration curve for the fluorescein concentration (FIG. 16). This curve suggests that the intensity measurements can be rather accurate. Using the concentration range from 0 to 6 $\mu M$, an uncertainly in the modulation of +/−0.007 results in a fluorescein concentration uncertainty of +/−0.1 $\mu M$. Hence, the intensity can be accurate to about one part in sixty, which is probably adequate for most clinical applications.

TABLE III

Global Intensity Decay Analysis of Fluorescein in 0.5% Intralipid - $[Ru(byp)_3]^{2-}$ Doped PVA Film System

| Concentration ($\mu$m) | $\tau_1$ = 3.89 ns | | $\tau_2$ = 1575 ns | | $\Delta t$ (ns) | $\tau_D$ (ns) | $\chi_R^2$ |
|---|---|---|---|---|---|---|---|
| | $\alpha_1$ | $f_1$ | $\alpha_2$ | $f_2$ | | | |
| 12 | 0.9996 | 0.871 | 0.0004 | 0.129 | 0.60 | 0.03 | 2.1 |
| 6 | 0.9994 | 0.792 | 0.0006 | 0.208 | | | |
| 3 | 0.9998 | 0.668 | 0.0012 | 0.332 | | | |
| 1.5 | 0.9970 | 0.449 | 0.0030 | 0.551 | | | |
| 0.75 | 0.9950 | 0.338 | 0.0050 | 0.662 | | | |

Examination of FIG. 16 reveals the modulation does not decrease linearly as the fluorescein concentration is decreased. This effect can be understood by noting that the modulation is approximately equal to the fractional intensity of the short component, $$m = \frac{f_S}{f_S + f_L}$$

One has to recall that the total intensity in a FD measurement is always normalized to unity, $f_S + f_L = 1.0$. A simple calculation reveals the origin of the non-linear dependence of the modulation on the total intensity. Suppose the initial intensity of the short component is $f_S = 0.9$, and that $f_L = 0.1$, resulting in a modulation of 0.9. Now suppose the intensity of the fluorescein emission is decreased two-fold. This can be simulated by setting $f_S = 0.45$ and $f_L = 0.1$, these values being appropriate prior to normalization. Hence, the two-fold decrease in fluorescein intensity results in a modulation near 0.81, consistent with the data in FIG. 16.

EXAMPLE 7 pH Sensing in Intralipid

Another use of modulation sensing is for measurement of the intensity of a sensing fluorophore in tissues or through skin. This was examined using 6-carboxy fluorescein. Fluorescein and its derivatives are well known to display intensities which depend on pH and dissociation of the carboxyl group (Thomas et al., 1979; Babcock, 1983; Klonis et al., 1998). The ionized form which exists at pH values above 7.5 is highly fluorescent, and the protonated low pH form is essentially non-fluorescent.

Figure 17:
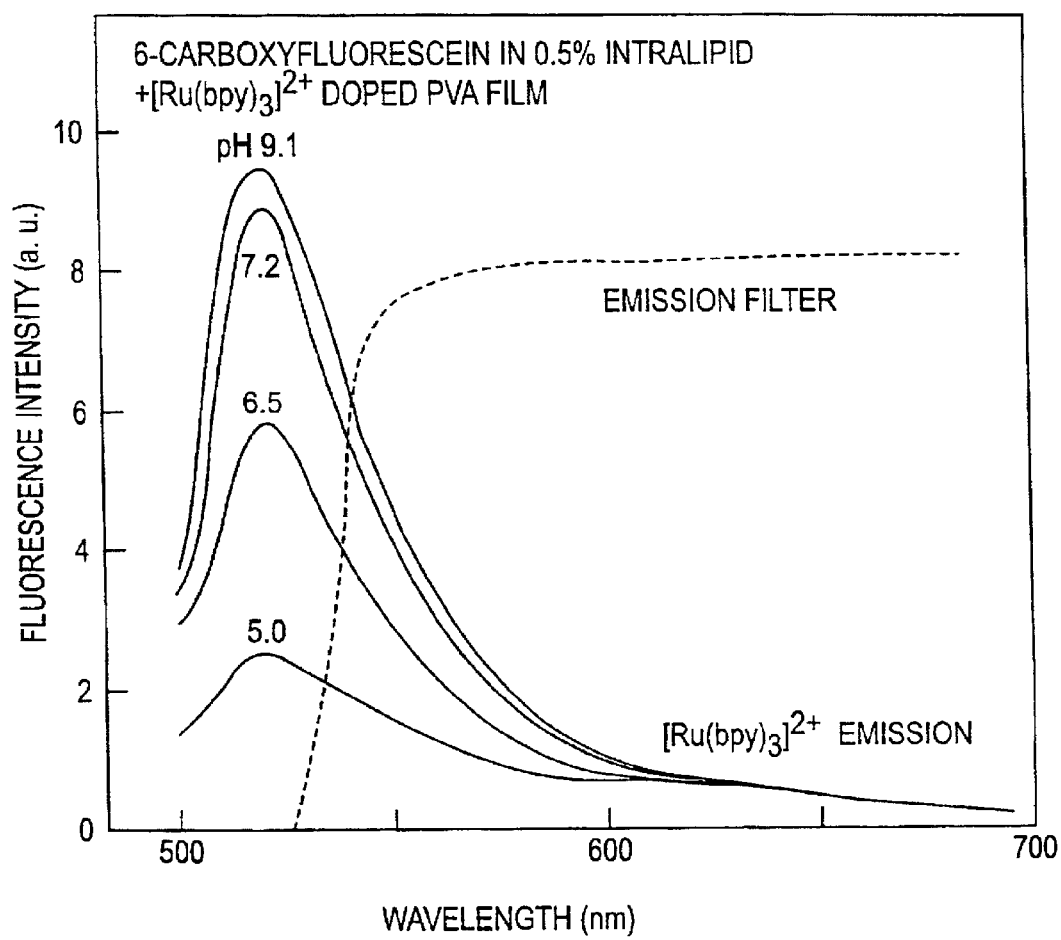
FIG. 17 shows emission spectra of 6carboxy fluorescein in 0.5% intralipid. The experimental arrangement is similar to that shown in FIG. 2, including the long-lifetime standard.
Figure 18A:
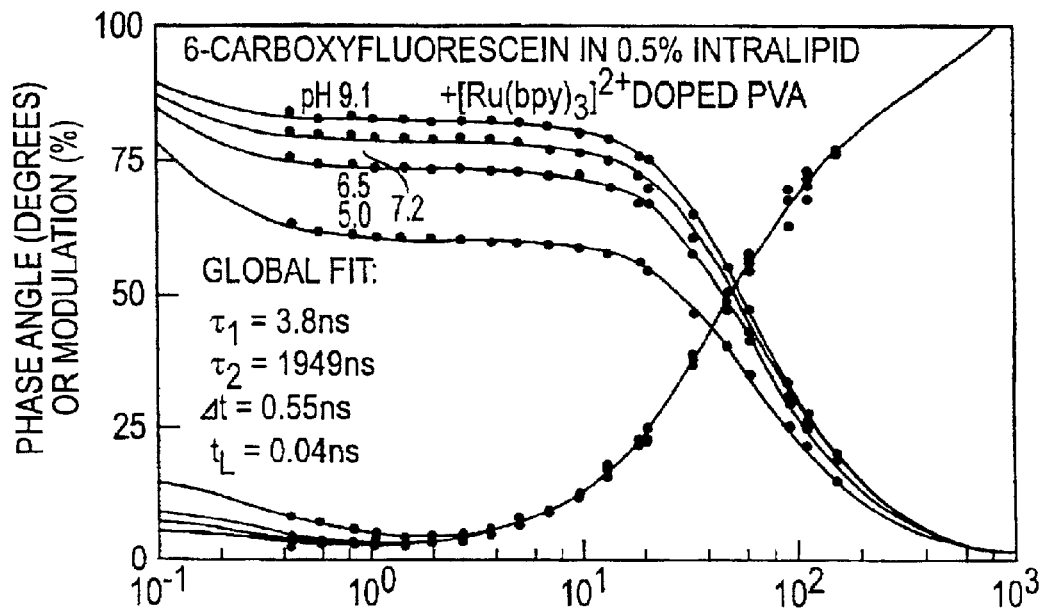
FIGS. 18A and 18B show the frequency response of the 6-carboxy fluorescein-[Ru(bpy)$_3$]$^{2+}$-intralipid sample shown in FIG. 6. The bottom panel shows the low frequency modulation on an expanded scale.
Figure 18B:
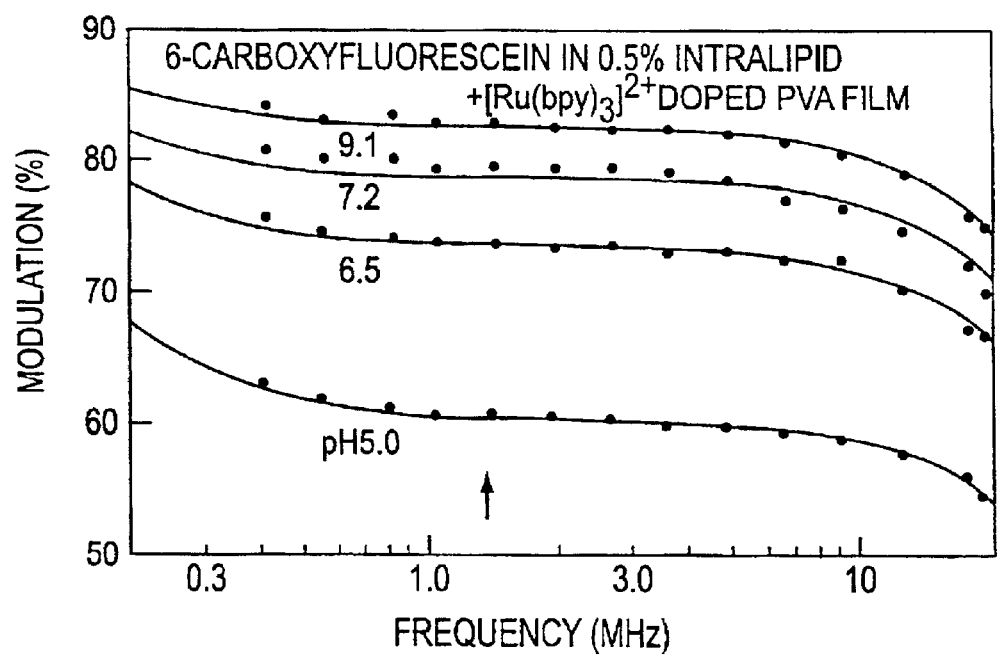
Figure 19:
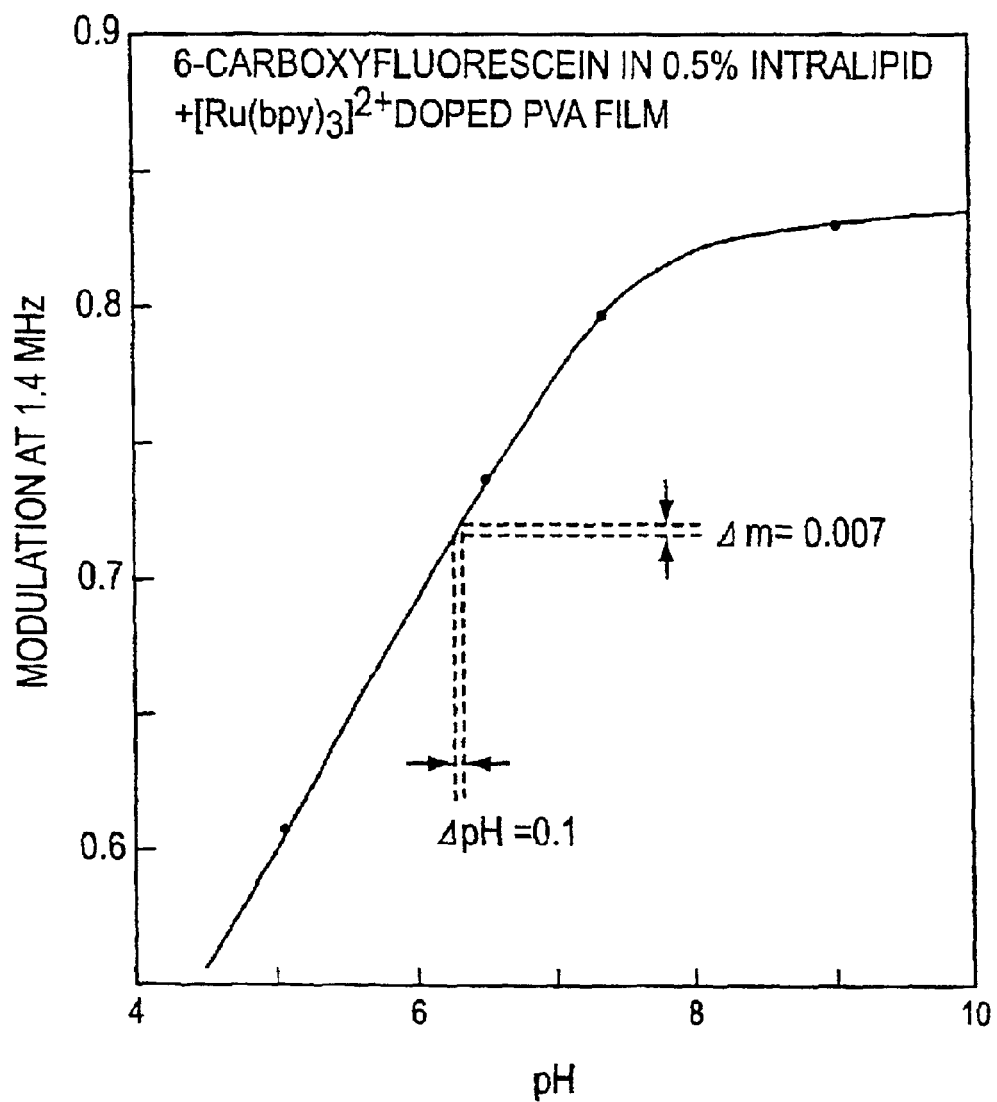
FIG. 19 shows modulation versus pH calibration curve for 6-CF in 0.5% intralipid.
Figure 20A:
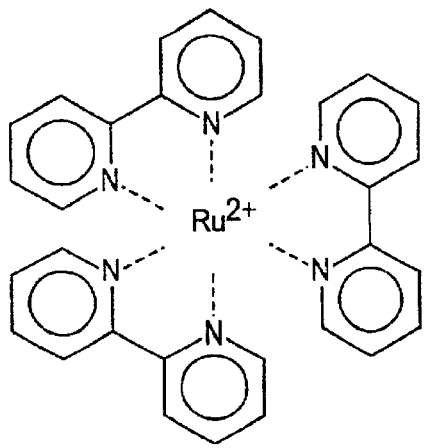
Figure 20B:
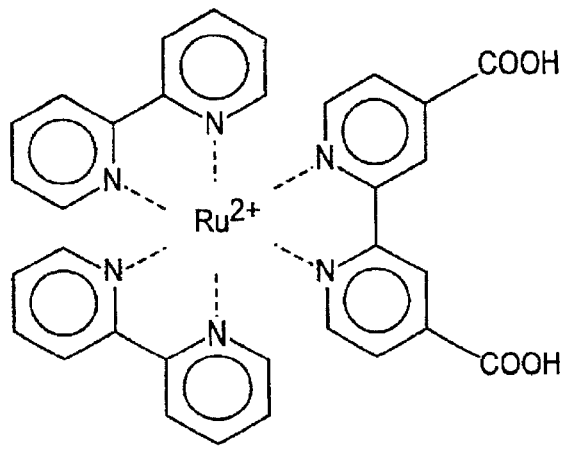
Figure 20C:
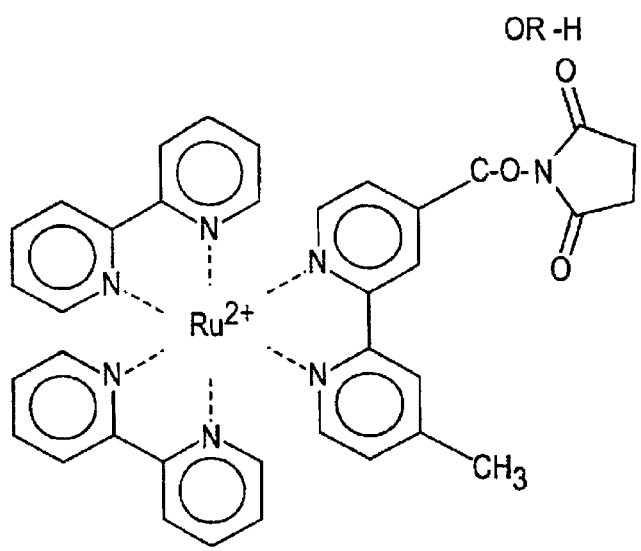
Figure 20G:
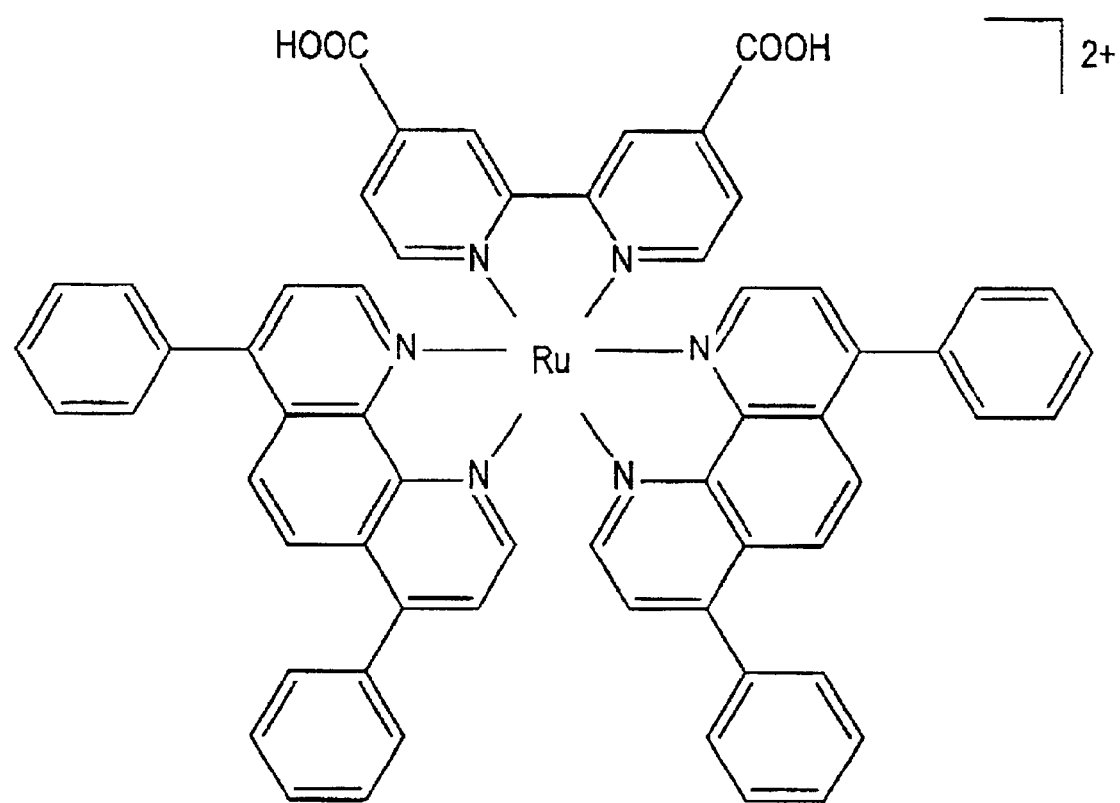
Figure 20H:
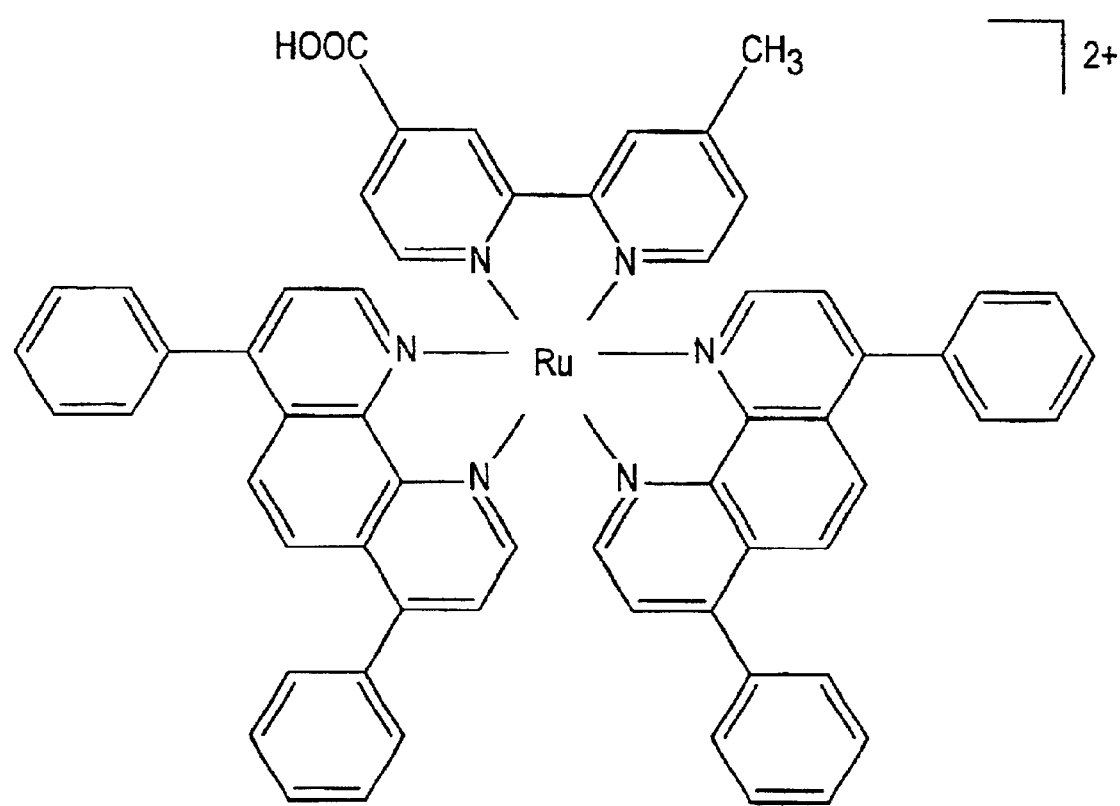
Figure 20I:
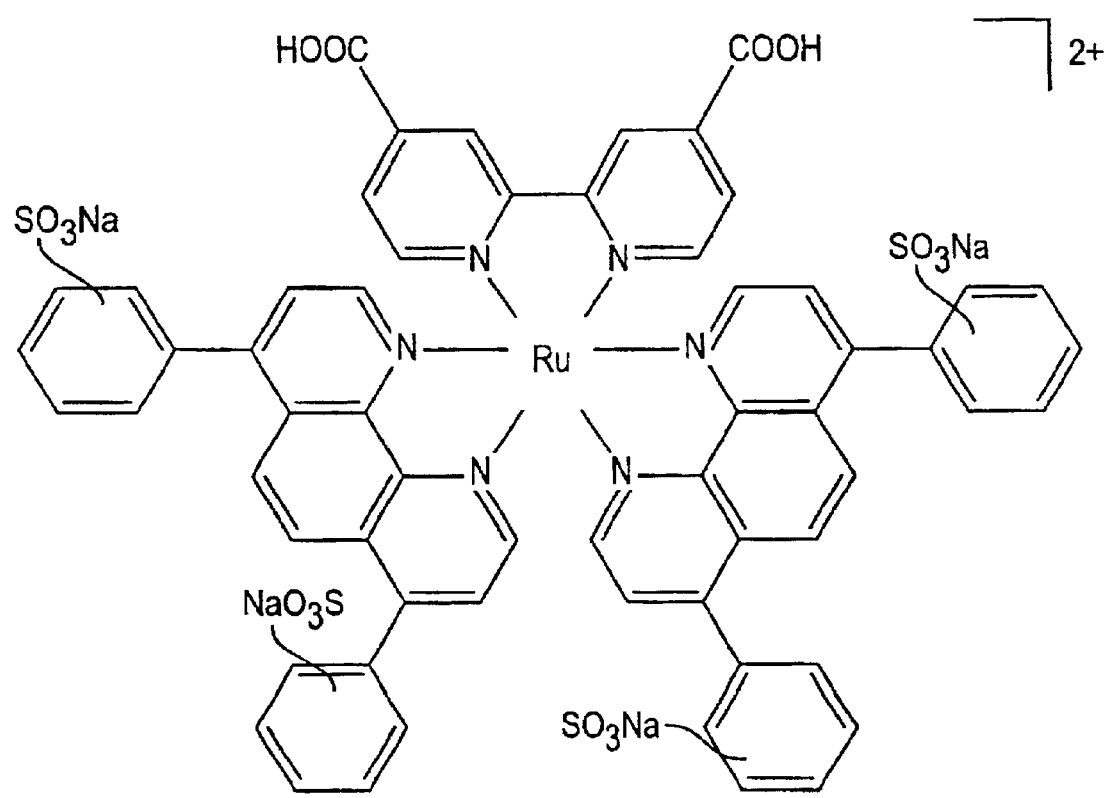
Figure 20J:
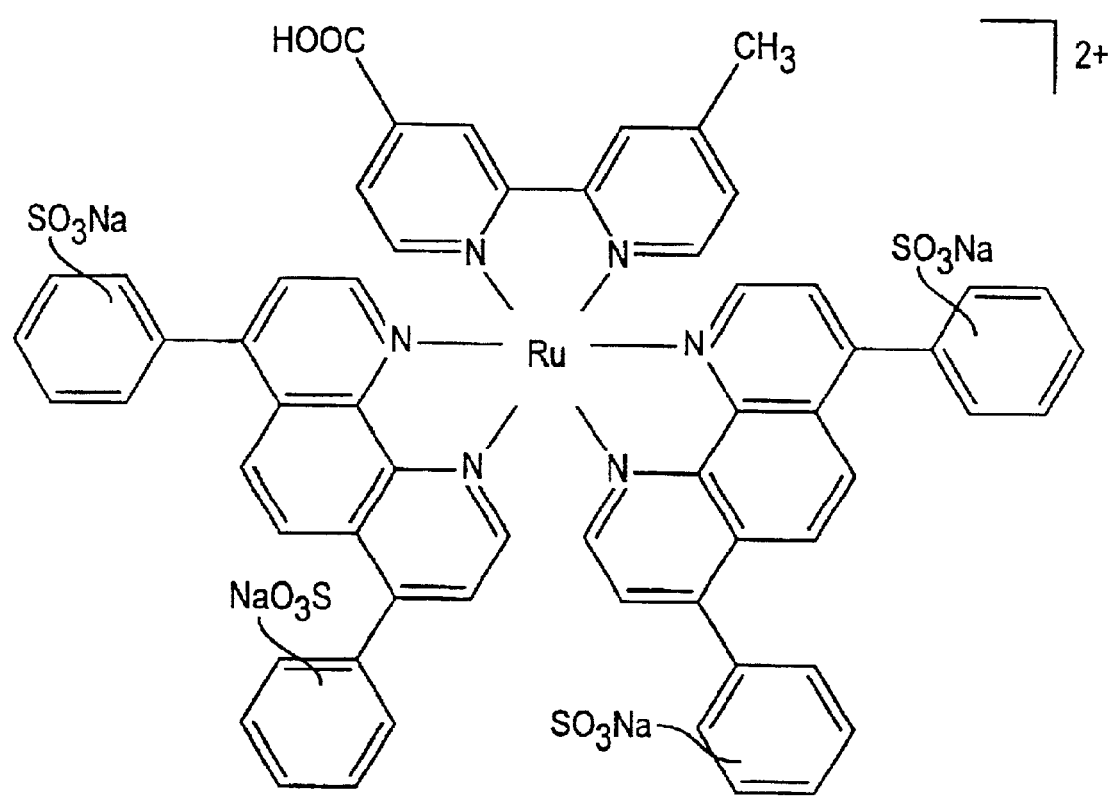
Figure 20K:
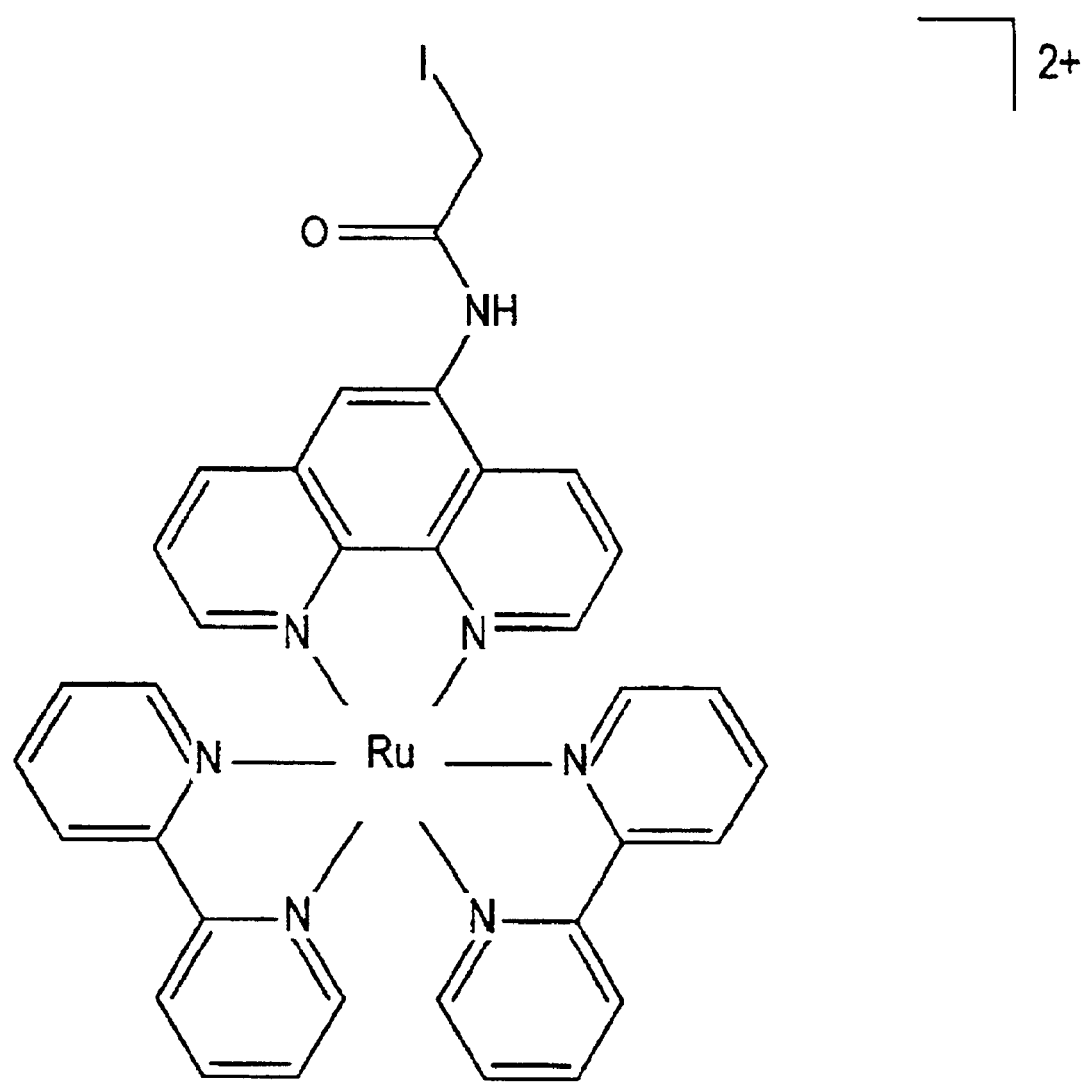
Figure 20L:
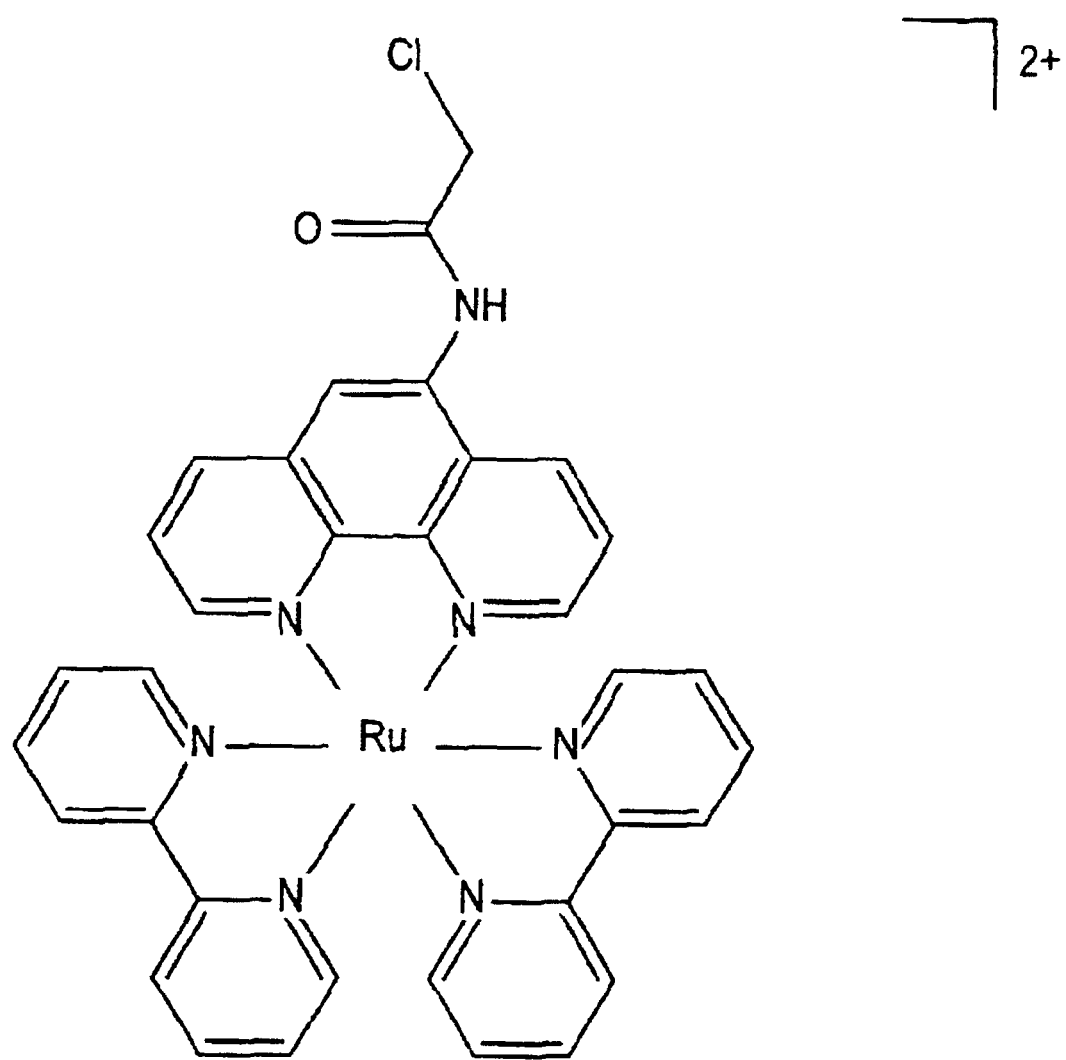
Figure 20E:
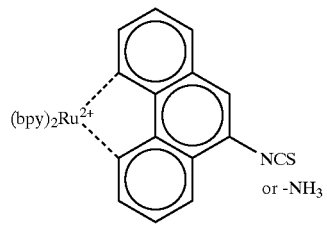
Figure 20F:
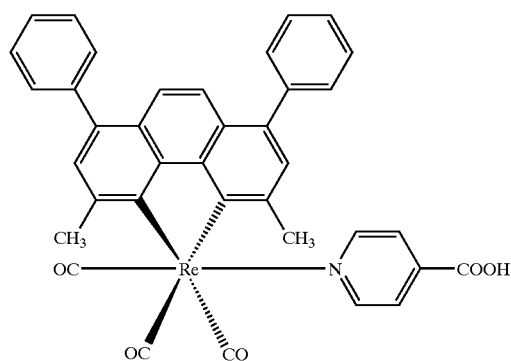
Figure 20G:
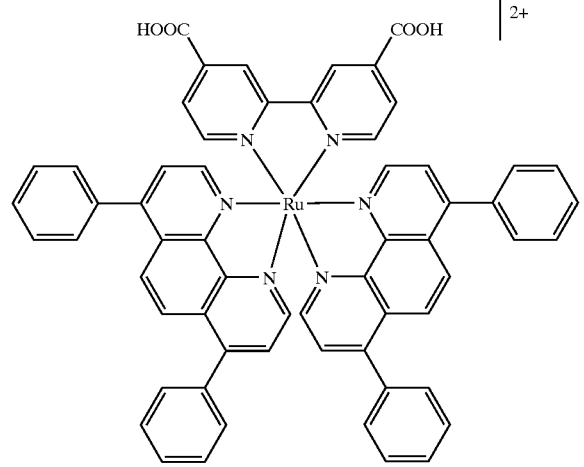
Figure 20H:
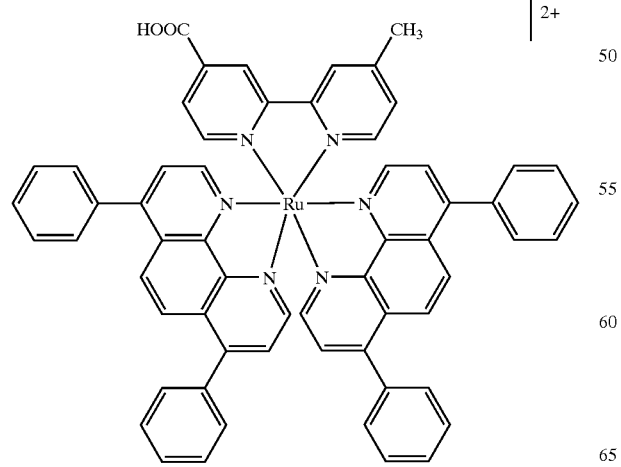
Figure 20I:
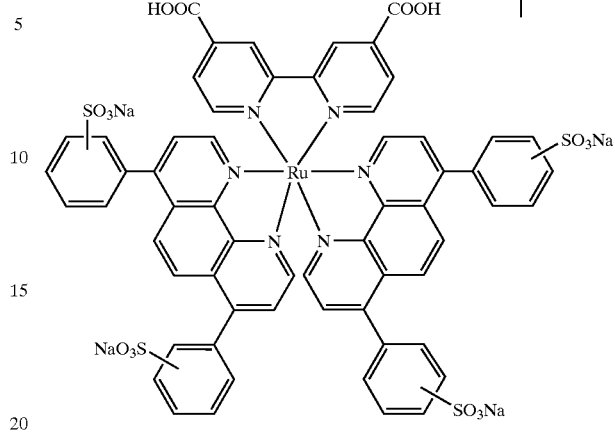
Figure 20J:
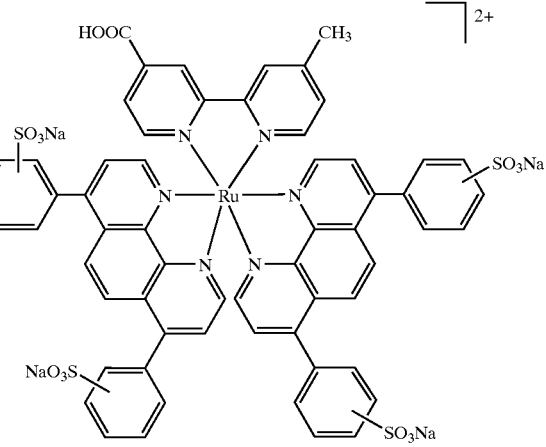
Figure 20K:
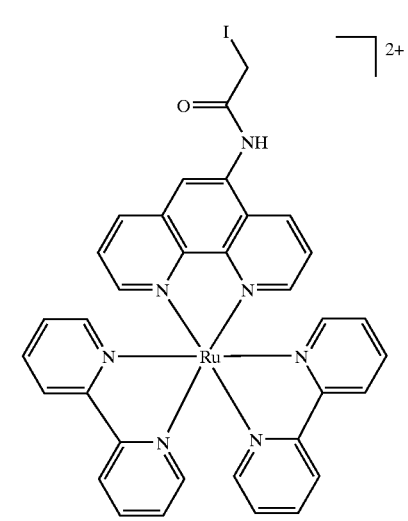

To test pH sensing in scattering media, 6-CF was diluted in 0.5% intralipid, and the long-lifetime reference was again on the outer surface of the cuvette. The emission spectra shows that the intensity of 6-CF decreases as the pH decreases (FIG. 17). The emission from $[Ru(bpy)_3]^{2+}$ in PVA film is centered near 600 nm and its intensity is independent of pH. The frequency responses for this pH sensor (FIGS. 18A and 18B) show that the modulation from 0.5 to 8 MHz is dependent on the pH of the intralipid solution. These modulation data were used to create a calibration curve for pH (FIG. 19). For this particular sensor. modulation values accurate to +/−0.007 result in an accuracy of +/−0.1 pH units. For clinical applications, pH values are typically accurate to +/−0.02 (Shapiro et al., 1993; Mahutte et al., 1994a; Mahutte, 1994). Optimization of the method will improve the accuracy of the method for such clinical applications.

TABLE IV

Global Intensity Decay Analysis of pH Sensor in 0.5% Intralipid

| pH | $\tau_1$ = 3.79 ns | | $\tau_2$ = 1949 ns | | $\Delta t$ (ns) | $\tau_D$ (ns) | $\chi_R^2$ |
|---|---|---|---|---|---|---|---|
| | $\alpha_1$ | $f_1$ | $\alpha_2$ | $f_2$ | | | |
| 9.1 | 0.9996 | 0.827 | 0.0004 | 0.173 | 0.55 | 0.04 | 5.4 |
| 7.2 | 0.9995 | 0.788 | 0.0005 | 0.212 | | | |
| 6.5 | 0.9993 | 0.735 | 0.0007 | 0.265 | | | |
| 5.0 | 0.9990 | 0.602 | 0.0010 | 0.398 | | | |

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

List of References

Akkaya, E. U., and Lakowicz, J. R. (1993). Styryl-based wavelength ratiometric probes: A new class of fluorescent calcium probes with long wavelength emission and a large Stokes' shift, *Anal. Biochem.* 213:285–289.

Babcock, D. F. (1983). Examination of the intracellular ionic environment and of ionophore action by null point measurements employing the fluorescein chromophore, *J. Biol. Chem.* 258:6380–6389.

Bambot, S. B., Rao, G., Romauld, M., Carter, G. M., Sipior, J., Terpetschnig, E., and Lakowicz, J. R. (1995). Sensing oxygen through skin using a red diode laser and fluorescence lifetime, *Biosensors & Bioelectronics* 10(6/7): 643–652.

Castellano, F. N., Dattelbaum, J. D., and Lakowicz, J. R. (1998). Long-lifetime Ru(II) complexes as labeling reagents for sulfhydryl groups, *Anal. Biochem.* 255:165–170.

Fraser, D. M., Ed. (1997). *Biosensors in the Body—Continuous in Vivo Monitoring*, Biomaterials Science and Engineering Series, Wiley, New York, pp. 268.

Gratton, E. and Limkeman, M. (1983). A Continuously Variable Frequency Cross-Correlation Phase Fluorometer with Picosecond Resolution, *Biophysics, J.* 44:315–324.

Gratton, E., Lakowicz, J. R., Maliwal, B., Cherek, H., Laczko, G., and Limkeman, M. (1984). Resolution of mixtures of fluorophores using variable-frequency phase and modulation data, *Biophys. J.* 46:479–486.

Gryczynski, I., Kusba, J., and Lakowicz, J. R. (1997). Effects of light quenching on the emission spectra and intensity decays of fluorophore mixtures, *J. Fluoresc.* 7(3):167–183.

Grynkiewicz, G., Poenie, M., and Tsien, R. Y. (1985). A new generation of $Ca^{2+}$ indicators with greatly improved fluorescence properties, *J. Biol. Chem.* 260(6):3440–3450.

Guo, X-G., Castellano, F. N., Li, L., Szmacinski, H., Lakowicz, J. R., and Sipior, J. (1997). A long-lived highly luminescent Re(I) metal-ligand complex as a biomolecular probe, *Anal. Biochem.* 254:179–186. Thomas, J. A., Buchsbaum, R. N., Zimniak, A., and Racker, E. (1979). Intracellular pH measurements in Ehrlich ascites tumor cells utilizing spectroscopic probes generated in situ, *Biochemistry* 18:2210–2218.

Guo, X-Q., Castellano, F. N., Li, L., and Lakowicz, J. R. (1998). Use of a long-lifetime Re(I) complex in fluorescence polarization immunoassays of high-molecular weight analytes, *Anal. Chem.* 70(3):632–637.

Harkins, A. B., Kurebayashi, N., and Baylor, S. M. (1993). Resting myoplasmic free calcium in frog skeletal muscle fibers estimated with Fluo-3, *Biophys. J.* 65:865–881.

Hirschfield, K. M., Toptygin, D., Packard, B. S., and Brand, L. (1993). Dynamic fluorescence measurements of two-state systems: Applications to calcium-chelating probes. *Anal. Biochem.* 209:209–218.

Hutchinson, C. L., Lakowicz, J. R. and Sevick-Muraca, E. M. (1995). Fluorescence Lifetime-Based Sensing in Tissues: A Computational Study, *Biophysical Journal* 68:1574–1582.

Kao, J. P. Y. (1994). Practical aspects of measuring $[Ca^{2+}]$ with fluorescent indicators in *Methods in Cell Biology*, Academic Press, New York, 40:155–181.

Kao, J. P. Y., Harootunian, A. T., and Tsien, R. Y. (1989). Photochemically generated cytosolic calcium pulses and their detection by Fluo-3, *J. Biol. Chem.* 264:8179–8184.

Kionis, N., Clayton, A. H. A., Voss, E. W., and Sawyer, W. H. (1998). Spectral properties of fluorescein in solvent-water mixtures: Applications as a probe of hydrogen bonding environments in biological systems, *Photochem. Photobiol.* 67:500–510.

Kunz, R. E., Ed. (1996). Part I: Plenary and Parallel Sessions; Part II: Poster Sessions, Proc. of 3rd European Conference on Optical Chemical Sensors and Biosensors, Europt(R)odeIII. *Sensors and Actuators B*, Elsevier Publishers, New York.

Lakowicz, J. R., Ed. (1994a). *Topics in Fluorescence Spectroscopy, Volume 4: Probe Design and Chemical Sensing*, Plenum Press, New York, pp. 501.

Lakowicz, J. R., Ed. (1994b). *Topics in Fluorescence Spectroscopy, Volume 4: Probe Design and Chemical Sensing*, Plenum Press, New York, pp. 183–222.

Lakowicz, J. R. (1999). *Principles of Fluorescence Spectroscopy*, 2nd Edition, Plenum Press, New York, in press.

Lakowicz, J. R., and Gryczynski, I. (1991). Frequency domain fluorescence spectroscopy in *Topics in Fluorescence Spectroscopy, Vol. 1: Techniques* (J. R Lakowicz, Ed.). Plenum Press, New York, pp. 293–331.

Lakowicz, J. R. and Maliwal, B. P. (1985). Construction and Performance of a Variable Frequency Phase-Modulation Fluorometer, *Biophys. J.* 46:463–377.

Lakowicz, J. R., and Szmacinski, H. (1992). Fluorescence lifetime-based sensing of pH, $Ca^{2+}$, $K^+$ and glucose, *Sensors and Actuators B* 11:133–143.

Lakowicz, J. R., Gratton, E., Laczko, G., Cherek, H., and Limkeman, M. (1984). Analysis of fluorescence decay kinetics from variable-frequency phase shift and modulation data, *Biophys. J.* 46:463–477.

Lakowicz, J. R., Szmacinski, H., and Johnson, M. L. (1992a). Calcium concentration imaging using fluorescence lifetime and long-wavelength probes *J. Fluoresc.* 2(1):47–62.

Lakowicz, J. R., Szmacinski, H., Nowaczyk, K., and Johnson, M. L. (1992b). Fluorescence lifetime imaging of calcium using Quin-2, *Cell Calcium* 13:131–147.

Lakowicz, J. R., Koen, P. A., Sznacinski, H., Gryczynski, 1., and Kuiba, J., (1994). Emerging biomedical applications of time-resolved fluorescence spectroscopy, *J. Fluoresc.* 4, 115–134.

Lakowicz, J. R., Terpetschnig, E., Szrnacinski, H., and Malak, H. (1995). Metal-ligand complexes as a new class of long-lived fluorophores for protein hydrodynamics and fluorescence polarization immunoassay, *SPIE Proc.* 2388:32–41.

Leznoff, C. C. and Lever A. B. P., Eds. (1989). Phthalocyanines Properties and Applications, VCH Publishers, New York, pp. 436.

Lippitsch, M. E., Pusterhofer, J., Leiner, M. J. P., and Wolfbeis, O. S. (1988). Fibre-optic oxygen sensor with the fluorescence decay time as the information carrier, *Anal. Chim. Acta* 205:1–6.

Lippitsch, M. E., Draxier, S., and Kieslinger, D. (1997). Luminescence lifetime-based sensing: new materials, new devices, *Sensors and Actuators B* 38-39:96–102.

Mahutte, C. K. (1994). Continuous intra-arterial blood gas monitoring, *Intensive Care Med.* 20:85–86.

Mahutte, C. K., Holody, M., Maxwell, T. P., Chen, P. A., and Sasse, S. A. (1994a). Development of a patient-dedicated, on-demand, blood gas monitor, *Am. J. Respir. Crit. Care. Med.* 149:852–859.

Mahutte, C. K., Sasse, S. A., Chen, and Holody, M. (1994b). Performance of a patient-dedicated, on-demand blood gas monitor in medical ICU patients, *Am. J. Respir. Med. Care Med.* 150:865–869.

Matsuoka, M., Ed. (1990). Infrared Absorbing Dyes, Plenum Press, New York, pp. 224.

Minta, A., Kao, J. P. Y., and Tsien, R. Y. (1989). Fluorescent indicators for cytosolic calcium based on rhodamine and fluorescein chromophores, *J. Biol. Chem.* 264:8171–8178.

Miyoshi, N., flara, K., Kimura, S., Nakanishi, K., and Fukuda, M. (1991). A new method of determining intracellular free $Ca^{2-}$ concentration using Quin-2 fluorescence, *Photochem. Photobiol.* 53(3):415–418.

Nuccitelli, F (Ed). *Methods in Cell Biology, Vol. 40: A Practical Guide to the Study of Calcium in Living Cells*, Academic Press, New York, pp. 368.

Oelkrug, D. (1994). "Fluorescence Spectroscopy in Turbid Media and Tissues," in *Topics in Fluorescence Spectroscopy: Vol4: Probe Design and Chemical Sensing* (J. R. Lakowicz, Ed.), Plenum Press, New York, pp. 223–253.

Randers-Eichhorn, L., Albano, C. R., Sipior, J., Bentley, W. E., and Rao, G. (1997). On-line green fluorescent protein sensor with LED excitation, *Biotech. Bioeng.* 55:921–926.

Schulman, S. G., Ed. (1993). *Molecular Luminescence Spectroscopy, Methods andApplications: Part 3*, John Wiley & Sons, Inc., New York, pp. 467.

Shapiro, B. A., Mahutte, C. K., Cane, R. D., and Gilmour, 1. J. (1993). Clinical performance of a blood gas monitor: A prospective, multicenter trial, *Crit. Care Med.* 21(4): 487–494.

Sipior, J., Carter, G. M., Lakowicz, J. R., and Rao, G. (1996). Single quantum well light emitting diodes demonstrated as excitation sources for nanosecond phase-modulation fluorescence lifetime measurements, *Rev. Sci. Instrum.* 67(11):3795–3798.

Sipior, J., Carter, G. M., Lakowicz, J. R., and Rao, G. (1997). Blue light-emitting diode demonstrated as an ultraviolet excitation source for nanosecond phase-modulation fluorescence lifetime measurements, *Rev. Sci. Instrum.* 68(7): 2666–2670.

Spichiger-Keller, U. E. (1998). *Chemical Sensors and Biosensors for Medical and Biological Applications*, Wiley-VCH, New York, pp. 413.

Szmacinski, H., and Lakowicz, J. R. (1994a). "Lifetiime-based sensing," in *Topics in Fluorescence Spectroscopy. Vol4: Probe Design and Chemical Sensing* (J. R. Lakowicz, Ed.), Plenum Press, New York, pp. 295–334.

Szmacinski, H. and Lakowicz, J. R. (1994b). Frequency-Domain Lifetime Measurements and Sensing in Highly Scattering Media, *Sensors and Actuators B* 30:207–215.

Szmacinski, H., and Lakowicz, J. R. (1996). Frequency-domain lifetime measurements and sensing in highly scattering media, *Sensors and Actuators* 30:207–215.

Terpetschnig, E., Szmacinski, H., and Lakowicz, J. R. (1997). Long-lifetime metal-ligand complexes as probes in biophysics and clinical chemistry, *Methods in Enzymology*, Academic Press, pp. 295–321.

Thomas, J. A., Buchsbaum, R. N., Zimniak, A., and Racker, E. (1979). Intracellular pH measurements in Ehrlich ascites tumor cells utilizing spectroscopic probes generated in situ, *Biochemistry* 18:2210–2218.

Thompson, R. B. (Ed.) (1997). *Advances in Fluorescence Sensing Technology III, SPIE Proc.*, Volume 2980, pp. 582.

Tsien, R. Y. (1989). Fluorescent indicators of ion concentrations in *Methods in Cell Biology*, Academic Press, New York, pp. 127–156.

Tsien, R Y., Rink, T. J., and Poenie, M. (1985). Measurement of cytosolic free $Ca^{2+}$ in individual small cells using fluorescence microscopy with dual excitation wavelengths, *Cell Calcium* 6:145–157.

Wolfbeis, O. S., Ed. (1991a). *Fiber Optic Chemical Sensors and Biosensors, Volume I*, CRC Press, Boca Raton, pp. 413.

Wolfbeis, O. S., Ed. (1991b). *Fiber Optic Chemical Sensors and Biosensors, Volume II*, CRC Press, Boca Raton, pp. 358.

What is claimed is:

1. A method of measuring a concentration of an analyte in a sample, wherein said method comprises:
   a) irradiating said sample with modulated incident light wherein said sample comprises a first fluorophore which absorbs a portion of said incident light and then emits emitted light, wherein the portion of said incident light absorbed by said first fluorophore is sensitive to the concentration of the analyte in the sample;
   b) allowing said emitted light to irradiate a second fluorophore;
   c) measuring light emitted from said sample;
   d) determining the phase angle or modulation of said light emitted from said sample; and
   e) correlating said phase angle or modulation to said concentration of said analyte,
   wherein in said first fluorophore has a decay time on a nanosecond timescale,
   wherein said second fluorophore has a decay time on a microsecond timescale.

2. The method of claim 1 wherein said modulated light is modulated at a frequency between 10 KHz and 100 MHz.

3. The method of claim 1 wherein said modulated light is modulated at a frequency between 50 KHz and 10 MHz.

4. The method of claim 1 wherein said modulated light is modulated at a frequency between 1 MHz and 10 MHz.

5. The method of claim 1 wherein said first fluorophore is a naturally occurring component of said sample.

6. The method of claim 1 wherein said first fluorophore is added to said sample.

7. The method of claim 1 wherein said second fluorophore is a naturally occurring component in said sample.

8. The method of claim 1 wherein said second fluorophore is added to said sample.

9. The method of claim 1 wherein said second fluorophore is separate from said sample.

10. The method of claim 1 wherein a probe for measuring said light emitted from said sample comprises said second fluorophore.

11. The method of claim 1 wherein said second fluorophore is on a container containing said sample.

12. The method of claim 1 wherein said analyte is in vivo, blood plasma, whole blood, saliva or body fluid.

13. The method of claim 12 wherein said second fluorophore is placed onto the outside of an organism comprising said analyte.

14. The method of claim 1 wherein said analyte is selected from the group consisting of $H^+$, pH, $Na^+$, $K^+$, $Li^+$, $Mg^{2+}$, $Ca^{2+}$, $Cl^-$, $HCO_3^-$, $CO_2$, $O_2$, glucose, lactate, an antigen and a drug.

15. The method of claim 1 wherein said first fluorophore is selected from the group consisting of Quin-2 (Glycine, N-(2-((8-(bis(carboxymethyl)amino)-6-methoxy-2-quinolinyl)methoxy)4-methylphenyl)-N-(carboxymethyl)-), Fura-2 (5-Oxazolecarboxylic acid, 2-(6-(bis (carboxymethyl)amino)-5-(2-(2-(bis(carboxymethyl) amino)-5-methylphenoxy)ethoxy)-2-benzofuranyl)-, pentapotassium salt], Indo-1 (1H-Indole-6-carboxylic acid, 2-[4-bis-(carboxymethyl)amino]-3-[2-[2-(bis-carboxymethyl)amino-5-methylphenoxy]ethoxy]phenyl]-, pentapotassium salt), Calcium Green (Glycine, N-[2-[2-[2-[bis(carboxymethyl)amino]-5-[[2',7'-dichloro-3',6'-dihydroxy-3-oxospiro[isobenzofuran-1(3H), 9'-[9H] xanthene)-5-yl]carbonyl]amino]phenoxy]ethoxy]phenyl]-N-(carboxymethyl)-, hexapotassium salt), Calcium Orange (Xanthylium, 9-[4-[[[[4-[bis[2-[(acetyloxy)methoxy]-2-oxoethyl]amino]-3-[2-[2-[bis[2-[(acetyloxy)methoxy]-2-oxoethyl]amino]phenoxy]ethoxy]phenyl]amino] thioxomethyl]amino]-2-carboxyphenyl]-3,6-bis (dimethylamino)-, inner salt), Calcium Crimson, Benzoxazine-crown, Mag-Quin-2, Magnesium Green (Glycine, N-[2-(carboxymethoxy)4-[[2',7'-dichloro-3',6'-dihydroxy-3-oxospiro[isobenzofuran-1(3H),9'-[9H] xanthen]-5-yl)carbonyl]amino]phenyl]-N-(carboxymethyl)-, pentapotassium salt), [[Benzoxazine-crown,]] PBFI (1,3-Benzenedicarboxylic acid, 4,4'-[1,4,10, 13-tetraoxa-7,16-diazacyclooctadecane-7,16-diylbis(5-methoxy-6,2-benzofurandiyl)]bis-), Sodium Green (Spiro [isobenzofuran-1(3H),9'-[9H]xanthene]-5-carboxamide, N,N$^+$-[1,4,10-trioxa-7,13-diazacyclopentadecane-7,13-diylbis(2,5-dimethoxy-4,1-phenylene)]bis[3',6'-bis (acetyloxy)-2',7'-dichloro-3-oxo), SNAFL-1 (Spiro[7H-benzo[c]xanthene-7,1'(3'H)-isobenzofuran]-ar'-carboxylic acid, 3,10-dihydroxy-3'oxo-), C. SNAFL-1, C. SNAFL-2, C. SNARF-1 (Benzenedicarboxylic acid, 2(or 4)-[10-(dimethylamino)-3oxo-3H-benzo[c]xanthene-7-yl]-), C. SNARF-2, C. SNARF-6, C. SNARF-X, BCECF (2',7'-bis-(2-carboxyethyl)-5-(and-6-)-carboxylfluorescein) Spiro (isobenzofuran-1(3H), 9'-(9H) xanthene)-2',7'-dipropanoic acid, ar-carboxy-3',6'-dihydroxy-3-oxo-), Resorufin Acetate (3H-Phenoxazin-3-one, 7-acetate-), 6-methoxy-N-ethylquinolinium chloride, N-(6-methoxyquinolyl) acetoethyl ester, 6-methoxy-N-ethylquinolinium chloride, 6-methoxy-N-(3-trimethylammoniumpropyl)quinolinium dibromide, 6-methoxy-N-(3-trimethylammoniumpropyl) phenanthrindium dibromide, 6-methoxy-N-(4-aminoalkyl) quinolinium, bromide hydrochloride, 6-methoxy-N-(3-sulfoproxyl)quinolinium N-sulfopropylacridinium, N,N'-dimethyl-9,9'-bisacridinium nitrate, N-methylacridinium-9-carboxamides, N-methylacridinium-9-methylcarboxylate, 8-hydroxypyrene-1,3,6-trisulfonate, [Ru(4,4'-diethylamin omethyl-2,2'-bipyridine)(2,2'-bipyridine)$_2$]$^{2+}$, Oregon Green Spiro[isobenzofuran-1(3H),9'-[9H]xanthen]-3-one, 2',7'-difluro-3',6'-dihydroxy-), DM-NERF Spiro(isobenzofuran-1 (3H),9'-(9H) xanthene)-ar-carboxylic acid, 2',7'-dimethyl-3'-ethylamino-6'-hydroxy-3-oxo-), Cl-NERF (Spiro (isobenzofuran-1(3H),9'-(9H) xanthene)-ar-carboxylic acid, 2'-chloro -6'-ethylamino-3'-hydroxy-7'-methyl-3-oxo-), Mag-Quin-1, Mag-Fura-2 (5-Oxazolecarboxylic acid, 2-[6-[bis(carboxymethyl)amino]-5-(carboxymethoxy)-2-benzofuranyl]-, tetrapotassium salt), Mag-Fura-5, Mag-Indo-1 (1H-Indole-6-carboxylic acid, 2-[4-[bis (carboxymethyl)amino]-3-(carboxymethoxy)phenyl]-, tetrapotassium salt), Mag-Fura-Red, Mg Orange (Xanthylium, 9-[4-[[[[3-carboxymethoxy4-(carboxymethyl)amino]phenyl]amino]thioxomethyl] amino]-2-carboxyphenyl]-3,6-bis(dimethylamino)-, tripotassium salt), sodium-binding benzofuran isophthalate, sodium-binding benzofuran oxazole, CD222, Fura Red (Glycine, N-[2-[(acetyloxy)methoxy]-2-oxoethyl]-N-[5-[2-[2-[bis[2-[(acetyloxy)methoxy]-2-oxoethyl]amino]-5-methylphenoxy]ethoxy]-2-[(5-oxo-2-thioxo4-imidazolidinylidene)methyl]-6-benzofuranyl]-, (acetyloxy) methyl) ester), BTC (coumarin benzothiazole-based indicator) (Glycine, N-[3-(2-benzothiazolyl)-6-[2[2-[bis (carboxymethyl)amino]-5-methylphenoxyl]ethoxy]-2-oxo-2H-1-benzopyran-7-yl]-N-(carboxymethyl)-, tetrapotassim salt), Fluo-3 (Glycine, N-[2-[[[[2-[bis(carboxymethyl) amino]-5-(2,7-dichloro-6-hydroxy-3-oxo-3H-xanthen-9-yl) phenoxy]methyl]methyl]oxy]-4-methylphenyl]-N-(carboxymethyl)-, pentammonium salt), Rhod-2 (Xanthylium, 9-[4-[bis[2-[(acetyloxy)methoxy]-2-oxoethyl] amino]-3-[2-[2-[bis[2-[(acetyloxy)methoxy]-2-oxoethyl] amino]phenoxy]ethoxy]phenyl]-3,6-bis(dimethylamino)-, bromide), Ca Green-2 (Glycine, N,N'-[1,2-ethanediylbis [oxy[4-[[(2',7'-dichloro-3',6'-dihydroxy-3-oxospiro [isobenzofuran-1(3H),9'-[9H]xanthen]-5-yl)carbonyl] amino]-2,1-phenyl]]]bis[N-(carboxymethyl)-, octapotassium salt), Ca Green-5N (Glycine, N-[2-[2-[2-[bis (carboxymethyl)amino]-5-[[(2',7'-dichloro-3',6'-dihydroxy-3-oxospiro[isobenzofuran-1(3H),9'-[9H]xanthen]-5-yl) carbonyl]amino]phenoxy]ethoxy]-4-nitrophenyl]-N-(carboxymethyl)-, hexapotassium salt) Ca Orange-5N (Xanthylium, 9-[4-[[[[4-[bis(carboxymethyl)amino]-3-[2-[2-[bis(carboxymethyl)amino]4-nitrophenoxy]ethoxy] phenyl]amino]thioxomethyl]amino]-2-carboxyphenyl]-3,6-bis(dimethylamino)-, tetrapotassium salt), Oregon Green—BAPTA-1 (Glycine, N-[2-[(acetyloxy)methoxy]-2-oxoethyl]-N-[4-[[[3',6'-bis(acetyloxy)-2',7'-difluoro-3-oxospiro[isobenzofuran-1(3H), 9'-[9H]xanthen]-5-yl] carbonyl]amino]-2-[2-[bis[2-[(acetyloxy)methoxy]-2-oxoethyl]amino]phenoxy]ethoxy]phenyl]-, (acetyloxy) methyl ester), BAPTA-2 1,2-bis[3',6'-bis(acetyloxy)-2',7'-difluoro-3-oxospiro[isobenzofuran-1(3H), 9'-[9H]xanthen]-5-yl]carbonyl]amino]-2-[2-[2-[bis[2-[(acetyloxy)methoxy]-2-oxoethyl]amino]phenoxy-ethan) and BAPTA-5N (Glycine, N-[2-[2-[2-[bis(carboxymethyl)amino]-5-[[(2',7'-difluoro-3',6'-dihydroxy-3-oxospiro[isobenzofuran-1(3H), 9'-[9H]xanthen]-5-yl) carbonyl]amino]phenoxy[ethoxy]4-nitrophenyl]-N-(carboxymethyl)-, hexapotassium salt).

16. The method of claim 1 wherein said second fluorophore is a compound selected from at least one of:

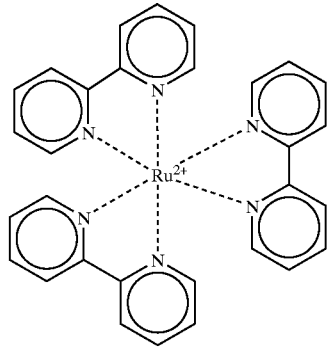

FIG. 20A

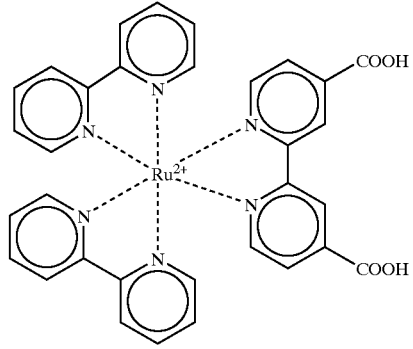

FIG. 20B

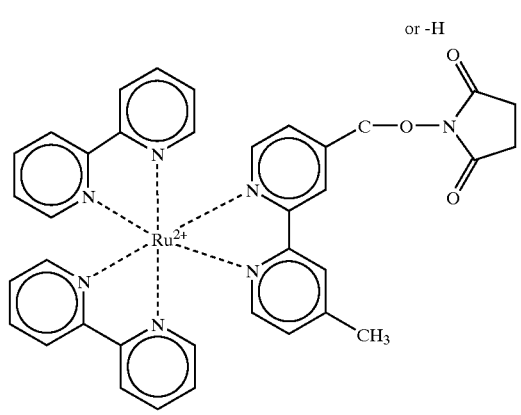

FIG. 20C or -H

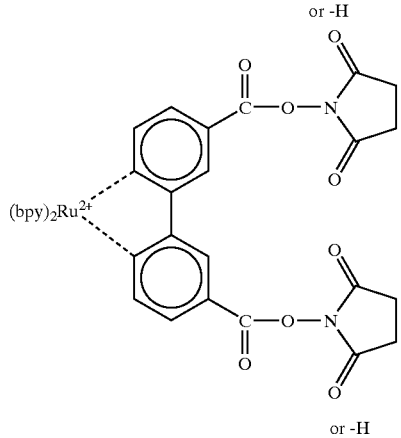

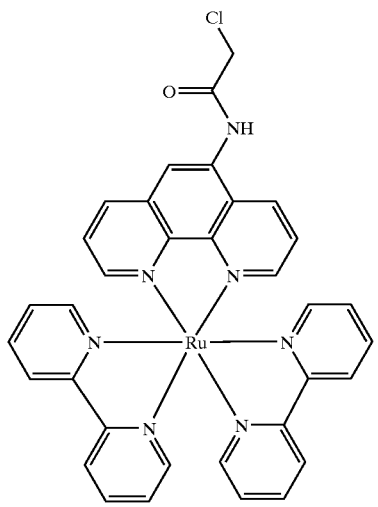

17. The method of claim 1 further comprising inserting a filter between said light emitted from said sample and a detector wherein the percentage of light emitted from said first fluorophore which is absorbed by said filter is different than the percentage of light emitted from said second fluorophore which is absorbed by said filter.

18. The method of claim 17 wherein the percentage of light emitted from said first fluorophore which is absorbed by said filter is greater than the percentage of light emitted from said second fluorophore which is absorbed by said filter.

19. The method of claim 17 wherein multiple measurements are made wherein measurements are made i) with different filters or ii) with one or more filters and with no filter.

20. The method of claim 1 wherein measuring is performed at more than one frequency.

21. The method of claim 1 wherein said sample comprises a light scattering medium.

22. The method of claim 21 wherein said light scattering medium is skin.

23. The method of claim 1 wherein said method is used clinically.

24. The method of claim 14, wherein said analyte is glucose, further wherein said second fluorophore is a glucose-sensitive fluorophore or a glucose-binding protein.

25. The method of claim 24 wherein said glucose-binding protein is a glucose-galactose binding protein or concanavalin A.

26. The method of claim 25 wherein said glucose-galactose binding protein or concanavalin A is labeled with a fluorophore.

27. The method of claim 14 wherein said analyte is an antigen or a drug, further wherein said second fluorophore is an antibody labeled with a fluorescent compound or said second fluorophore is an antibody fragment labeled with a fluorescent compound.

28. The method of claim 14 wherein said analyte is lactate, further wherein said second fluorophore is a lactate-specific fluorophore or a lactate binding protein labeled with a fluorescent compound.

29. The method of claim 1 wherein said incident light is produced by a laser, a light emitting diode (LED) or an electroluminescent light source (ELL).

30. The method of claim 1 wherein said sample is from a tissue culture or an aquarium.

31. The method of claim 1 wherein said method is used to monitor a bioprocessing reaction.

32. The method of claim 1 wherein said method is used as a part of an analytical chemistry process.

33. The method of claim 1 wherein said method is used industrially or in process control.

34. The method of claim 1 wherein said first fluorophore is said analyte.

35. The method of claim 1, wherein the detected emission of said first and second fluorophores is equivalent to a fraction of a total emission of the first fluorophore.

36. The method of claim 35, wherein said light is modulated at a frequency between 50 kHz and 10 MHz.

37. The method of claim 1, wherein the first fluorophore exhibits no lifetime change in presence of the analyte.

38. The method of claim 36, wherein measuring is performed at more than one frequency.

* * * * *

UNITED STATES PATENT AND TRADEMARK OFFICE
CERTIFICATE OF CORRECTION

PATENT NO. : 6,806,089 B1
APPLICATION NO. : 09/786627
DATED : October 19, 2004
INVENTOR(S) : Joseph R. Lakowicz and Ignacy Gryczynski It is certified that error appears in the above-identified patent and that said Letters Patent is hereby corrected as shown below:

Col. 1, line 9, delete "may have" and insert --has--; delete "this" and insert --the--.

Signed and Sealed this

Sixth Day of May, 2008

JON W. DUDAS
*Director of the United States Patent and Trademark Office*